(12) United States Patent
Gaiba et al.

(10) Patent No.: US 8,293,798 B2
(45) Date of Patent: Oct. 23, 2012

(54) COMPOUNDS

(75) Inventors: Alessandra Gaiba, Harlow (GB); Susan Roomans, Harlow (GB); Martin Edward Swarbrick, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 357 days.

(21) Appl. No.: 12/740,216

(22) PCT Filed: Oct. 30, 2008

(86) PCT No.: PCT/EP2008/064700
§ 371 (c)(1),
(2), (4) Date: Apr. 28, 2010

(87) PCT Pub. No.: WO2009/056582
PCT Pub. Date: May 7, 2009

(65) Prior Publication Data
US 2010/0305166 A1 Dec. 2, 2010

(30) Foreign Application Priority Data
Nov. 2, 2007 (GB) .................................. 0721611.2

(51) Int. Cl.
| | |
|---|---|
| *A01N 37/18* | (2006.01) |
| *A01N 43/40* | (2006.01) |
| *A61K 31/165* | (2006.01) |
| *A61K 31/435* | (2006.01) |
| *C07C 233/00* | (2006.01) |
| *C07C 235/00* | (2006.01) |
| *C07C 237/00* | (2006.01) |
| *C07D 213/00* | (2006.01) |

(52) U.S. Cl. ............. 514/622; 514/277; 564/161; 546/1
(58) Field of Classification Search .................. 514/622, 514/277; 564/161; 546/1
See application file for complete search history.

(56) References Cited

U.S. PATENT DOCUMENTS
2005/0267170 A1   12/2005   Koike et al.

OTHER PUBLICATIONS

Database CHEMCATS [Online], Chemical Abstracts Service, Columbus, Ohio, U.S., Abstract XP002513963, Nov. 2008.
Database CHEMCATS [Online], Chemical Abstracts Service, Columbus, Ohio, U.S., Abstract XP002513964, Oct. 2008.
Database CHEMCATS [Online], Chemical Abstracts Service, Columbus, Ohio, U.S., Abstract XP002513965, Nov. 2008.

*Primary Examiner* — Shengjun Wang
*Assistant Examiner* — Kendra D Carter
(74) *Attorney, Agent, or Firm* — Bonnie L. Deppenbrock

(57) ABSTRACT

A compound of formula (I) or salts thereof,

Formula (I)

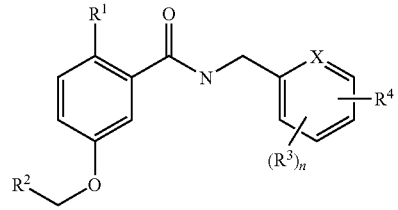

wherein $R^1$, $R^2$, $R^3$, $R^4$, n and X are as defined in the specification; a process for preparing such compounds, a pharmaceutical composition comprising such compounds; and the use of such compounds in medicine.

5 Claims, No Drawings

COMPOUNDS

CROSS-REFERENCE TO RELATED APPLICATIONS

This application is filed pursuant to 35 U.S.C. §371 as a United States National Phase Application of International Patent Application Ser. No. PCT/EP2008/064700 filed Oct. 30, 2008, which claims priority from Great Britain Application No. 0721611.2 filed in the United Kingdom on Nov. 2, 2007, the contents of which are incorporated herein by reference.

FIELD OF THE INVENTION

This invention relates to benzamide derivatives, to processes for their preparation, to pharmaceutical compositions containing them and to their use in medicine.

BACKGROUND OF THE INVENTION

The compounds of the present invention are $EP_4$ receptor agonists.

A number of review articles describe the characterization and therapeutic relevance of the prostanoid receptors as well as the most commonly used selective agonists and antagonists: *Eicosanoids; From Biotechnology to Therapeutic Applications*, Folco, Samuelsson, Maclouf, and Velo eds, Plenum Press, New York, 1996, chap. 14, 137-154 and Journal of Lipid Mediators and Cell Signalling, 1996, 14, 83-87 and *Prostanoid Receptors, Structure, Properties and Function*, S Narumiya et al, Physiological Reviews 1999, 79(4), 1193-126.

The $EP_4$ receptor is a 7-transmembrane receptor and its natural ligand is the prostaglandin $PGE_2$. $PGE_2$ also has affinity for the other EP receptors (types $EP_1$, $EP_2$ and $EP_3$). The prostanoid $EP_4$ receptor falls into a group of receptors normally associated with elevation of intracellular cyclic adenosine monophosphate (cAMP) levels. The $EP_4$ receptor is associated with smooth muscle relaxation, intraocular pressure, pain (in particular inflammatory, neuropathic and visceral pain), inflammation, neuroprotection, lymphocyte differentiation, bone metabolic processes, allergic activities, promotion of sleep, renal regulation, gastric or enteric mucus secretion and duodenal bicarbonate secretion. The $EP_4$ receptor plays an important role in closure of the ductus arteriosus, vasodepression, inflammation and bone remodeling as reviewed by Narumiya in *Prostaglandins & Other Lipid Mediators* 2002, 68-69 557-73.

A number of publications have demonstrated that $PGE_2$ acting through the $EP_4$ receptor subtype, and $EP_4$ agonists alone, can regulate inflammatory cytokines after an inflammatory stimulus. Takayama et al in the *Journal of Biological Chemistry* 2002, 277(46), 44147-54 showed $PGE_2$ modulates inflammation during inflammatory diseases by suppressing macrophage derived chemokine production via the $EP_4$ receptor. In *Bioorganic & Medicinal Chemistry* 2002, 10(7), 2103-2110, Maruyama et al demonstrate the selective $EP_4$ receptor agonist (ONO-AE1-437) suppresses LPS induced TNF-α in human whole blood whilst increasing the levels of IL-10. An article from *Anesthesiology*, 2002, 97, 170-176 suggests that a selective $EP_4$ receptor agonist (ONO-AE1-329) effectively inhibited mechanical and thermal hyperalgesia and inflammatory reactions in acute and chronic monoarthritis.

Two independent articles from Sakuma et at in *Journal of Bone and Mineral Research* 2000, 15(2), 218-227 and Miyaura et at in *Journal of Biological Chemistry* 2000, 275 (26), 19819-23, report impaired osteoclast formation in cells cultured from $EP_4$ receptor knock-out mice. Yoshida et al in *Proceedings of the National Academy of Sciences of the United States of America* 2002, 99(7), 4580-4585, by use of mice lacking each of the $PGE_2$ receptor EP subtypes, identified $EP_4$ as the receptor that mediates bone formation in response to $PGE_2$ administration. They also demonstrated a selective $EP_4$ receptor agonist (ONO-4819) consistently induces bone formation in wild type mice. Additionally, Terai et al in *Bone* 2005, 37(4), 555-562 have shown the presence of a selective $EP_4$ receptor agonist (ONO-4819) enhanced the bone-inducing capacity of rhBMP-2, a therapeutic cytokine that can induce bone formation.

Further research by Larsen et al shows the effects of $PGE_2$ on secretion in the second part of the human duodenum is mediated through the $EP_4$ receptor (*Acta. Physiol. Scand.* 2005, 185, 133-140). Also, it has been shown a selective $EP_4$ receptor agonist (ONO-AE1-329) can protect against colitis in rats (Nitta et al in *Scandinavian Journal of Immunology* 2002, 56(1), 66-75).

Doré et al in *The European Journal of Neuroscience* 2005, 22(9), 2199-206 have shown that $PGE_2$ can protect neurons against amyloid beta peptide toxicity by acting on $EP_2$ and $EP_4$ receptors. Furthermore Doré has demonstrated in *Brain Research* 2005, 1066(1-2), 71-77 that an $EP_4$ receptor agonist (ONO-AE1-329) protects against neurotoxicity in an acute model of excitotoxicity in the brain.

Woodward et al in Journal of Lipid Mediators 1993, 6(1-3), 545-53 found intraocular pressure could be lowered using selective prostanoid agonists. Two papers in Investigative Ophthalmology & Visual Science have shown the prostanoid $EP_4$ receptor is expressed in human lens epithelial cells (Mukhopadhyay et at 1999, 40(1), 105-12), and suggest a physiological role for the prostanoid $EP_4$ receptor in modulation of flow in the trabecular framework of the eye (Hoyng et at 1999, 40(11), 2622-6).

Compounds exhibiting $EP_4$ receptor binding activity and their uses have been described in, for example, WO98/55468, WO00/18744, WO00/03980, WO00/15608, WO00/16760, WO00/21532, WO0/1010426, EP0855389, EP0985663, WO02/047669, WO02/50031, WO02/50032, WO02/50033, WO02/064564, WO03/103604, WO03/077910, WO03/086371, WO04/037813, WO04/067524, WO04/085430, U.S. Ser. No. 04/142,969, WO05/021508, WO05/105733, WO05/105732, WO05/080367, WO05/037812, WO05/116010, WO06/122403, WO07/088189 and WO07/088190.

SUMMARY OF THE INVENTION

The present invention provides compounds of formula (I) or salts thereof,

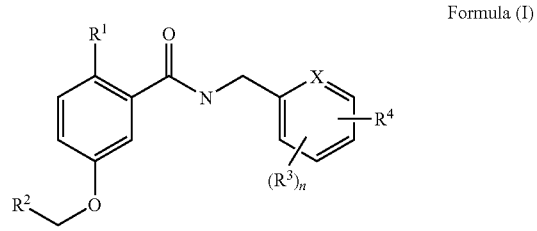

Formula (I)

wherein
R¹ represents H, or halo or $C_{1-4}$ alkyl;
R² represents a 4 to 6 membered non-aromatic carbocylic group, or phenyl, or pyridinyl;
which carbocylic or pyridinyl group is optionally substituted with one or two substituents, which may be the same or different, selected from the group consisting of:
halo, $C_{1-4}$ alkyl, $C_{1-4}$ alkoxy, halo $C_{1-4}$ alkyl or halo $C_{1-4}$ alkoxy;
or which phenyl group is substituted with one or two substituents, which may be the same or different, selected from the group consisting of: halo, $C_{1-4}$ alkyl, $C_{1-4}$ alkoxy, halo $C_{1-4}$ alkyl or halo $C_{1-4}$ alkoxy;
R³ represents halo;
R⁴ represents COOH, $CH_2COOH$ or tetrazolyl;
X represents C or N; and
n is 0 or 1;
with the proviso that:
when R⁴ is in the 4 position on the ring, it cannot be $CH_2COOH$; and
when R⁴ is in the 3 position on the ring, R² is not 4-chlorophenyl.

DETAILED DESCRIPTION OF THE INVENTION

In one embodiment of the invention R¹ is chloro. In another embodiment of the invention R¹ is methyl. In another embodiment of the invention R¹ is fluoro.

In one embodiment of the invention R² is phenyl. In another embodiment of the invention R² is phenyl substituted in the 3 position with halo, $C_{1-4}$ alkyl, $C_{1-4}$ alkoxy, halo $C_{1-4}$ alkyl or halo $C_{1-4}$ alkoxy.

In one embodiment of the invention R² is chlorophenyl. In another embodiment of the invention R² is 2-chlorophenyl. In a further embodiment of the invention R² is 3-chlorophenyl. In a still further embodiment of the invention R² is 4-chlorophenyl.

In one embodiment of the invention R² is fluorophenyl. In another embodiment of the invention R² is 3-flurophenyl.

In one embodiment of the invention R² is difluorophenyl. In another embodiment of the invention R² is 3,5-difluorophenyl.

In one embodiment of the invention R² is methylphenyl. In another embodiment of the invention R² is 3-methylphenyl.

In one embodiment of the invention R² is methyloxyphenyl. In another embodiment of the invention R² is 3-methyloxyphenyl.

In one embodiment of the invention R² is cyclohexane. In another embodiment of the invention R² is cyclobutane.

In one embodiment of the invention R² is trifluoromethylphenyl. In another embodiment of the invention R² is 3-trifluoromethylphenyl.

In one embodiment of the invention R² is pyridinyl. In another embodiment of the invention R² is 3-pyridinyl. In a further embodiment of the invention R² is 2-pyridinyl.

In one embodiment of the invention R² is methylpyridinyl. In a further embodiment of the invention R² is 2-methylpyridinyl. In a still further embodiment of the invention R² is 6-methyl-pyridinyl.

In one embodiment of the invention R³ is fluoro. In a further embodiment of the invention R³ is in the 4 position.

In one embodiment of the invention R⁴ is COOH. In a further embodiment of the invention R⁴ is COOH in the 3 position. In a still further embodiment of the invention R⁴ is COOH is in the 4 position.

In one embodiment of the invention R⁴ is $CH_2COOH$. In a further embodiment of the invention R⁵ is $CH_2COOH$ in the 3 position.

In one embodiment of the invention R⁴ is tetrazolyl. In a further embodiment of the invention R⁴ is terazolyl in the 4 position.

In one embodiment of the invention R⁴ is COOH in the 4 position and n is 0.

In one embodiment of the invention X is C.
In one embodiment of the invention X is N.
In one embodiment of the invention R¹ is chloro, and R² is chlorophenyl. In a further embodiment of the invention R¹ is chloro, and R² is 3-chlorophenyl. In a still further embodiment of the invention R¹ is chloro, R² is 3-chlorophenyl and X is C. In a yet further embodiment of the invention R¹ is chloro, R² is 3-chlorophenyl, X is C and n is 0. In another embodiment of the invention R¹ is chloro, R² is 3-chlorophenyl, X is C, n is 0 and R⁴ is $CH_2COOH$. In yet another embodiment of the invention R¹ is chloro, R² is 3-chlorophenyl, X is C, n is 0 and R⁴ is $CH_2COOH$ in the 3 position.

In one embodiment of the invention X is C, R¹ is chloro, n is 0 and R⁴ is COOH. In another embodiment of the invention X is C, R¹ is chloro, n is 0, and R⁴ is COOH in the 4 position. In a further embodiment of the invention X is C, R¹ is chloro, n is 0, R⁴ is COOH in the 4 position and R² is trifluromethylphenyl. In a still further embodiment of the invention X is C, R¹ is chloro, n is 0, R⁴ is COOH in the 4 position and R² is 3-trifluromethylphenyl.

In one embodiment of the invention the compound of formula (I) is selected from the group consisting of:
4-({[(2-chloro-5-{[(2-chlorophenyl)methyl]oxy}phenyl)carbonyl]amino}methyl)benzoic acid;
4-({[(2-chloro-5-{[(3-chlorophenyl)methyl]oxy}phenyl)carbonyl]amino}methyl)benzoic acid;
3-({[(2-chloro-5-{[(3-chlorophenyl)methyl]oxy}phenyl)carbonyl]amino}methyl)benzoic acid;
6-({[(2-chloro-5-{[(3-chlorophenyl)methyl]oxy}phenyl)carbonyl]amino}methyl)-3-pyridinecarboxylic acid;
4-({[(5-{[(3-chlorophenyl)methyl]oxy}-2-methylphenyl)carbonyl]amino}methyl)benzoic acid;
5-({[(2-chloro-5-{[(3-chlorophenyl)methyl]oxy}phenyl)carbonyl]amino}methyl)-2-fluorobenzoic acid;
[3-({[(2-chloro-5-{[(3-chlorophenyl)methyl]oxy}phenyl)carbonyl]amino}methyl)phenyl]acetic acid;
4-({[(5-{[(3-chlorophenyl)methyl]oxy}-2-fluorophenyl)carbonyl]amino}methyl)benzoic acid;
4-({[(2-chloro-5-{[(3-fluorophenyl)methyl]oxy}phenyl)carbonyl]amino}methyl)benzoic acid;
4-({[(2-chloro-5-{[(3-methylphenyl)methyl]oxy}phenyl)carbonyl]amino}methyl)benzoic acid;
4-({[(2-chloro-5-{[(4-chlorophenyl)methyl]oxy}phenyl)carbonyl]amino}methyl)benzoic acid;
4-{[({2-chloro-5-[(cyclohexylmethyl)oxy]phenyl}carbonyl)amino]methyl}benzoic acid;
4-{[({2-chloro-5-[(cyclobutylmethyl)oxy]phenyl}carbonyl)amino]methyl}benzoic acid;
6-({[(5-{[(3-chlorophenyl)methyl]oxy}-2-methylphenyl)carbonyl]amino}methyl)-3-pyridinecarboxylic acid;
[3-({[(5-{[(3-chlorophenyl)methyl]oxy}-2-methylphenyl)carbonyl]amino}methyl)phenyl]acetic acid;
3-({[(5-{[(3-chlorophenyl)methyl]oxy}-2-methylphenyl)carbonyl]amino}methyl)benzoic acid;
6-({[(5-{[(4-chlorophenyl)methyl]oxy}-2-methylphenyl)carbonyl]amino}methyl)-3-pyridinecarboxylic acid;
3-({[(2-chloro-5-{[(2-chlorophenyl)methyl]oxy}phenyl)carbonyl]amino}methyl)benzoic acid;

3-({[(5-{[(2-chlorophenyl)methyl]oxy}-2-methylphenyl)carbonyl]amino}methyl)benzoic acid;
4-[({[2-chloro-5-({[3-(methyloxy)phenyl]methyl}oxy)phenyl]carbonyl}amino)methyl]benzoic acid;
4-({[(2-chloro-5-{[(3,5-difluorophenyl)methyl]oxy}phenyl)carbonyl]amino}methyl)benzoic acid;
4-({[(5-{[(3-fluorophenyl)methyl]oxy}-2-methylphenyl)carbonyl]amino}methyl)benzoic acid;
4-({[(2-methyl-5-{[(3-methylphenyl)methyl]oxy}phenyl)carbonyl]amino}methyl)benzoic acid;
4-[({[2-chloro-5-({[3-(trifluoromethyl)phenyl]methyl}oxy)phenyl]carbonyl}amino)methyl]benzoic acid;
6-({[(2-chloro-5-{[(2-chlorophenyl)methyl]oxy}phenyl)carbonyl]amino}methyl)-3-pyridinecarboxylic acid;
4-({[(2-chloro-5-{[(2-methyl-3-pyridinyl)methyl]oxy}phenyl)carbonyl]amino}methyl)benzoic acid;
[3-({[(2-methyl-5-{[(3-methylphenyl)methyl]oxy}phenyl)carbonyl]amino}methyl)phenyl]acetic acid;
4-({[(2-chloro-5-{[(6-methyl-2-pyridinyl)methyl]oxy}phenyl)carbonyl]amino}methyl)benzoic acid;
[3-({[(5-{[(3-fluorophenyl)methyl]oxy}-2-methylphenyl)carbonyl]amino}methyl)phenyl]acetic acid;
2-chloro-5-{[(3-chlorophenyl)methyl]oxy}-N-{[4-(1H-tetrazol-5-yl)phenyl]methyl}benzamide;
4-{[({2-methyl-5-[(phenylmethyl)oxy]phenyl}carbonyl)amino]methyl}benzoic acid; and
4-{[({2-fluoro-5-[(phenylmethyl)oxy]phenyl}carbonyl)amino]methyl}benzoic acid.

As used herein, the term 'C$_{1-4}$ alkyl' includes straight chain and branched chain alkyl groups containing 1 to 4 carbon atoms, such as methyl, ethyl, n-propyl, iso-propyl, n-butyl and 2-methylpropyl.

As used herein, the term 'C$_{1-4}$ alkoxy' includes those with straight and branched chains containing 1 to 4 carbon atoms, such as methyloxy, ethyloxy, n-propyloxy, iso-propyloxy, n-butyloxy and 2-methylpropyloxy.

As used herein, the term 'halo C$_{1-4}$ alkyl' includes straight and branched chain alkyl groups containing 1 to 4 carbon atoms substituted by one or more halo atoms, for example trifluromethyl, difluoromethyl, trifluoro ethyl and difluoroethyl.

As used herein, the term 'halo C$_{1-4}$ alkoxy' includes straight and branched chain alkoxy groups substituted by one or more halo atoms, for example trifluromethyloxy difluoromethyloxy, trifluoroethyloxy and difluoroethyloxy.

As used herein, the term "a 4 to 6 membered non-aromatic carbocyclic group" means cyclobutly, cyclopentyl or cyclohexyl.

As used herein, the term halo means fluoro, chloro, bromo, or iodo.

As used herein, the term tetrazolyl includes all tautomeric forms.

For the avoidance of doubt, as used herein, with respect to R$^3$ and R$^4$ the term "in the 3 position" means in the position marked 3 in the Formula (Z), and the term "in the 4 position" means in the position marked 4 in the Formula (Z).

Formula (Z)

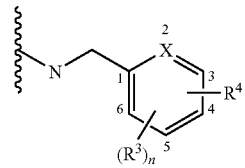

The numbering on the R2 ring follows conventional numbering well known to the skilled person.

It is to be understood that the present invention encompasses pharmaceutically acceptable derivatives of the compounds of formula (I), by which is meant any pharmaceutically acceptable salt, solvate or ester, or salt or solvate of such ester of the compounds of formula (I), or any other compound which upon administration to the recipient is capable of providing (directly or indirectly) a compound of formula (I) or an active metabolite or residue thereof.

It will be appreciated that, for pharmaceutical use, the salts referred to above will be the pharmaceutically acceptable salts, but other salts may find use, for example in the preparation of compounds of formula (I) and the pharmaceutically acceptable salts thereof.

Pharmaceutically acceptable salts include those described by Berge, Bighley and Monkhouse, *J. Pharm. Sci.*, 1977, 66, 1-19. The term "pharmaceutically acceptable salts" refers to salts prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic bases include salts of primary, secondary, and tertiary amines; substituted amines including naturally occurring substituted amines; and cyclic amines. Particular pharmaceutically acceptable organic bases include arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, procaine, purines, theobromine, triethylamine, trimethylamine, tripropyl amine, tris(hydroxymethyl)aminomethane, and the like. Salts may also be formed from basic ion exchange resins, for example polyamine resins.

It will be appreciated that the compounds of formula (I) may be produced in vivo by metabolism of a suitable prodrug. Such prodrugs may be for example physiologically acceptable metabolically labile esters of compounds of formula (I). These may be formed by esterification of the carboxylic acid group in the parent compound of formula (I) with, where appropriate, prior protection of any other reactive groups present in the molecule followed by deprotection if required. Examples of such metabolically labile esters include C$_{1-4}$alkyl esters e.g. methyl ethyl or t-butyl esters esters, C$_{3-6}$ alkenyl esters e.g. allyl substituted or unsubstituted aminoalkyl esters (e.g. aminoethyl, 2-(N,N-diethylamino)ethyl, or 2-(4-morpholino)ethyl esters or acyloxyalkyl esters such as, acyloxymethyl or 1-acyloxyethyl e.g. pivaloyloxymethyl, 1-pivaloyloxyethyl, acetoxymethyl, 1-acetoxyethyl,1-(1-methoxy-1-methyl)ethylcarbonyloxyethyl, 1-benzoyloxyethyl, isopropoxycarbonyloxymethyl, 1-isopropoxycarbonyloxyethyl, cyclohexylcarbonyloxymethyl, 1-cyclohexylcarbonyloxyethyl ester, cyclohexyloxycarbonyloxymethyl, 1-cyclohexyloxycarbonyloxyethyl, 1-(4-tetrahydropyranyloxy)carbonyloxyethyl or 1-(4-tetrahydropyranyl)carbonyloxyethyl.

It is to be understood that the present invention encompasses all isomers of the compounds of formula (I) and their pharmaceutically acceptable derivatives, including all geometric, tautomeric and optical forms, and mixtures thereof (e.g. racemic mixtures).

Since the compounds of formula (I) are intended for use in pharmaceutical compositions, it will be understood that they are each provided in substantially pure form, for example at least 50% pure, at least 75% pure and at least 95% pure (% are on a wt/wt basis). Impure preparations of the compounds of formula (I) may be used for preparing the more pure forms used in the pharmaceutical compositions. Although the purity of intermediate compounds of the present invention is less critical, it will be readily understood that the substantially pure form is preferred as for the compounds of formula (I). Whenever possible, the compounds of the present invention are obtained in crystalline form.

When some of the compounds of this invention are allowed to crystallise or are recrystallised from organic solvents, solvent of crystallisation may be present in the crystalline product. This invention includes within its scope such solvates, including solvates of the free acid molecule and solvates of salts derived from the free acid molecule. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. This invention also includes within its scope anhydrous forms of the compounds of formula (I).

In addition, different crystallisation conditions may lead to the formation of different polymorphic forms of crystalline products. This invention includes within its scope all polymorphic forms of the compounds of formula (I).

The present invention also includes within its scope all isotopically-labelled compounds of formula (I). Such compounds are identical to those recited above except that one or more atoms therein are replaced by an atom having an atomic mass or mass number different from the atomic mass or mass number usually found in nature. Examples of isotopes that can be incorporated into compounds of formula (I) and pharmaceutically acceptable derivatives thereof include isotopes of hydrogen, carbon, nitrogen, oxygen and fluorine, such as 2H, 3H, 11C, 13C, 14C, 15N, 17O, 18O and 18F.

Isotopically-labelled compounds of formula (I), for example those into which radioactive isotopes such as 3H, 14C are incorporated, are useful in drug and/or substrate tissue distribution assays. Tritiated, i.e., 3H, and carbon-14, i.e., 14C, isotopes are particularly preferred for their ease of preparation and detectability. 11C and 18F isotopes are particularly useful in PET (positron emission tomography), and are useful in brain imaging. Further substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labelled compounds of formula (I) may be prepared by carrying out the synthetic procedures disclosed in the Schemes and/or in the Examples below, by substituting a readily available isotopically labelled reagent for a non-isotopically labelled reagent.

The compounds of formula (I) are $EP_4$ receptor agonists and may therefore be useful in treating $EP_4$ receptor mediated diseases.

In particular the compounds of formula (I) may be useful in the treatment of pain, for example, chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds of formula (I) may be particularly useful in the treatment of neuropathic pain and symptoms associated therewith. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. Symptoms of neuropathic pain include spontaneous shooting and lancinating pain, or ongoing, burning pain. In addition, there is included pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of formula (I) may also be useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease, diarrhoea, constipation); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome.

The compounds of formula (I) may also be useful in the treatment of immunological diseases such as autoimmune diseases, immunological deficiency diseases or organ transplantation. The compounds of formula (I) may also be effective in increasing the latency of HIV infection.

The compounds of formula (I) may also be useful in the treatment of diseases of excessive or unwanted platelet activation such as intermittent claudication, unstable angina, stroke, and acute coronary syndrome (e.g. occlusive vascular diseases).

The compounds of formula (I) may also be useful as a drug with diuretic action, or may be useful to treat overactive bladder syndrome.

The compounds of formula (I) may also be useful in the treatment of impotence or erectile dysfunction.

The compounds of formula (I) may also be useful in the treatment of bone disease characterised by abnormal bone metabolism or resorption such as osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, calculosis, lithiasis (especially urolithiasis), gout and ankylosing spondylitis, tendinitis and bursitis.

The compounds of formula (I) may also be useful in bone remodelling and/or promoting bone generation and/or promoting fracture healing.

The compounds of formula (I) may also be useful for attenuating the hemodynamic side effects of NSAIDs and COX-2 inhibitors.

The compounds of formula (I) may also be useful in the treatment of cardiovascular diseases such as hypertension or myocardial ischemia; functional or organic venous insufficiency; varicose therapy; haemorrhoids; and shock states associated with a marked drop in arterial pressure (e.g. septic shock).

The compounds of formula (I) may also be useful in the treatment of neurodegenerative diseases such as dementia, particularly degenerative dementia (including senile dementia, Alzheimer's disease, Pick's disease, Huntingdon's chorea, Parkinson's disease and Creutzfeldt-Jakob disease, Amyotrophic lateral sclerosis (ALS), motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds of formula (I) may also be useful in the treatment of neurological disorders and may be useful as neuroprotecting agents. The compounds of the invention may also be useful in the treatment of neurodegeneration following stroke, cardiac arrest, pulmonary bypass, traumatic brain injury, spinal cord injury or the like.

The compounds of formula (I) may also be useful in the treatment of complications of Type 1 diabetes (e.g. diabetic microangiopathy, diabetic retinopathy, diabetic nephropathy, macular degeneration, glaucoma), nephrotic syndrome, aplastic anaemia, uveitis, Kawasaki disease and sarcoidosis.

The compounds of formula (I) may also be useful in the treatment of a kidney dysfunction (nephritis, particularly mesangial proliferative glomerulonephritis, nephritic syndrome), a liver dysfunction (hepatitis, cirrhosis) and gastrointestinal dysfunction (diarrhoea).

It is to be understood that as used herein any reference to treatment includes both treatment of established symptoms and prophylactic treatment.

In a further embodiment the invention, there is provided a compound of formula (I) or a pharmaceutically acceptable salt thereof for use in human or veterinary medicine.

In a yet further embodiment of the invention, there is provided a compound of formula (I) or a pharmaceutically acceptable salt thereof for use in the treatment of a condition which is mediated by the action, or loss of action, of $PGE_2$ at $EP_4$ receptors.

In a still further embodiment of the invention, there is provided a method of treating a human or animal subject suffering from a condition which is mediated by the action, or by loss of action, of $PGE_2$ at $EP_4$ receptors which comprises administering to said subject an effective amount of a compound of formula (I) or a pharmaceutically acceptable salt thereof.

In another embodiment of the invention there is provided a method of treating a human or animal subject suffering from a pain, or an inflammatory, immunological or bone disease, a neurodegenerative disease or a kidney dysfunction, which method comprises administering to said subject an effective amount of a compound of formula (I) or a pharmaceutically acceptable salt thereof.

In one embodiment of the invention, there is provided the use of a compound of formula (I) or a pharmaceutically acceptable salt thereof for the manufacture of a medicament for the treatment of a condition which is mediated by the action or loss of action of $PGE_2$ at $EP_4$ receptors.

In a further embodiment of the invention there is provided the use of a compound of formula (I) or a pharmaceutically acceptable salt thereof for the manufacture of a medicament for the treatment or prevention of a condition such as a pain, or an inflammatory, immunological, bone, neurodegenerative or kidney disorder.

The compounds of formula (I) and their pharmaceutically acceptable salts are conveniently administered in the form of pharmaceutical compositions. Such compositions may conveniently be presented for use in conventional manner in admixture with one or more physiologically acceptable carriers or excipients.

Thus, in another aspect of the invention, there is provided a pharmaceutical composition comprising a compound of formula (I) or a pharmaceutically acceptable salt thereof adapted for use in human or veterinary medicine.

While it is possible for the compounds of formula (I) or a pharmaceutically acceptable salt thereof to be administered as the raw chemical, it is preferable to present it as a pharmaceutical formulation. The formulations of the present invention comprise the compounds of formula (I) or a pharmaceutically acceptable salt thereof together with one or more acceptable carriers or diluents therefor and optionally other therapeutic ingredients. The carrier(s) must be "acceptable" in the sense of being compatible with the other ingredients of the formulation and not deleterious to the recipient thereof.

Thus, in one embodiment the invention provides a pharmaceutical composition comprising a compound of formula (I) or a pharmaceutically acceptable salt thereof and a pharmaceutically acceptable carrier or diluent therefor.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy (see for example methods disclosed in 'Remington—The Science and Practice of Pharmacy', 21$^{st}$ Edition, Lippincott, Williams & Wilkins, USA, 2005 and references therein). All methods include the step of bringing into association the compound of formula (I) or a pharmaceutically acceptable salt thereof ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds of formula (I) may also be formulated as depot preparations. Such long acting formulations may be administered by implantation (for example subcutaneously or intramuscularly) or by intramuscular injection. Thus, for example, the compounds of formula (I) may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

The compounds of formula (I) may be used in combination with other therapeutic agents, for example COX-2 inhibitors, such as celecoxib, rofecoxib, valdecoxib or parecoxib; 5-lipoxygenase inhibitors; analgesics such as paracetamol; NSAID's, such as diclofenac, indomethacin, nabumetone, naproxen or ibuprofen; leukotriene receptor antagonists; DMARD's such as methotrexate; sodium channel blockers, such as lamotrigine; N-type calcium channel antagonists; NMDA receptor modulators, such as glycine receptor antagonists; gabapentin, pregabalin and related compounds; tricyclic antidepressants such as amitriptyline; neurone stabilising antiepileptic drugs; mono-aminergic uptake inhibitors such as venlafaxine; opioid analgesics; local anaesthetics; $5HT_1$ agonists, such as triptans, for example sumatriptan, naratriptan, zolmitriptan, eletriptan, frovatriptan, almotriptan or rizatriptan; $EP_1$ receptor ligands; $EP_2$ receptor ligands; $EP_3$ receptor ligands; $EP_1$ antagonists; $EP_2$ antagonists and $EP_3$ antagonists; cannabanoid receptor agonists; VR1 antagonists. When the compounds are used in combination with other therapeutic agents, the compounds may be administered either sequentially or simultaneously by any convenient route.

The invention thus provides, in a further embodiment, a combination comprising a compound of formula (I) or a pharmaceutically acceptable salt thereof together with a further therapeutic agent or agents. In one embodiment of the invention there is provided a combination comprising a compound of formula (I) or a pharmaceutically acceptable salt thereof and paracetamol.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. In particular there is provided a pharmaceutical composition comprising a compound of formula (I) or a pharmaceutically acceptable salt thereof, paracetamol and a pharmaceutically acceptable carrier or diluent therefore. The individual components of such combinations may be administered either sequentially or simultaneously in separate or combined pharmaceutical formulations.

When a compound of formula (I) or a pharmaceutically acceptable salt thereof is used in combination with a second therapeutic agent active against the same disease, the dose of each compound may differ from that when the compound is used alone. Appropriate doses will be readily appreciated by those skilled in the art.

In one embodiment of the invention there is provided a method of treating a human or animal subject suffering from a condition which is mediated by the action, or by loss of action, of $PGE_2$ at $EP_4$ receptors which comprises administering to said subject an effective amount of a compound of formula (I) or a pharmaceutically acceptable salt thereof and paracetamol.

A proposed daily dosage of compounds of formula (I) or their pharmaceutically acceptable salts for the treatment of man is from 0.001 to 30 mg/kg body weight per day and more particularly 0.1 to 3 mg/kg body weight per day, calculated as the free acid, which may be administered as a single or divided dose, for example one to four times per day. The dose range for adult human beings is generally from 0.1 to 1000 mg/day, such as from 10 to 800 mg/day, preferably 10 to 200 mg/day, calculated as the free acid.

A suitable daily dosage of paracetamol is up to 4000 mg per day. Suitable unit doses include 200, 400, 500 and 1000 mg, one, two, three or four times per day.

The precise amount of the compounds of formula (I) administered to a host, particularly a human patient, will be the responsibility of the attendant physician. However, the dose employed will depend on a number of factors including the age and sex of the patient, the precise condition being treated and its severity, the route of administration, and any possible combination therapy that may be being undertaken.

The present invention provides a process for preparing the compounds of formula (I) and pharmaceutically acceptable derivatives thereof.

Thus, in one embodiment there is provided a process for preparing a compound of formula (I), where $R^4$ is not tetrazolyl, or a pharmaceutically acceptable derivative thereof, which process comprises reacting a compound of formula (II),

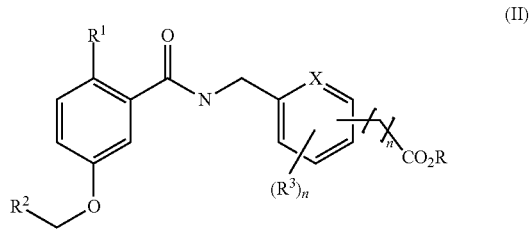

wherein, $R^1$, $R^2$, $R^3$, and X are as defined in formula (I), n is 0 or 1 and R represents a suitable alkyl ester protecting group, such as a methyl, ethyl or benzyl group, with an aqueous acid, and optionally thereafter forming a pharmaceutically acceptable derivative of the compound so formed.

A suitable acid is 2N hydrochloric acid. The above-mentioned reaction involving a compound of formula (II) and an acid may be conveniently carried out in a solvent such as acetic acid, at an elevated temperature, for example 90° C.

In a further embodiment of the invention there is provided a process for preparing a compound of formula (I), where $R^4$ is not tetrazolyl, or a pharmaceutically acceptable derivative thereof, which process comprises reacting a compound of formula (II),

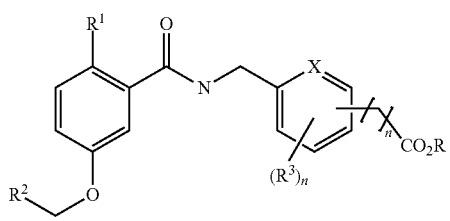

(II)

wherein, $R^1$, $R^2$, $R^3$, and X are as defined in formula (I), n is 0 or 1 and R represents a suitable alkyl ester protecting group, such as a methyl, ethyl or benzyl group, with an aqueous base, and optionally thereafter forming a pharmaceutically acceptable derivative of the compound so formed.

Suitable bases include sodium hydroxide and lithium hydroxide. The above-mentioned reaction involving compound (II) and a base may be conveniently carried out in a solvent or a mixture of solvents, such as methanol/water, ethanol/water or 1,4-dioxane/water. The reaction may be performed at ambient or an elevated temperature.

Compounds of formula (II) may be prepared according to Scheme 1 below:

Scheme 1

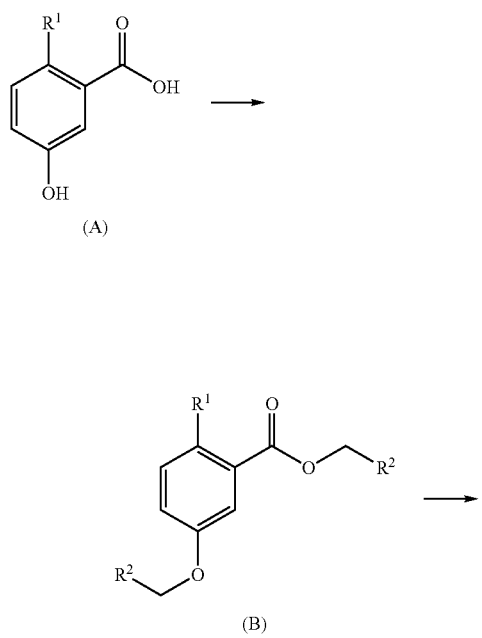

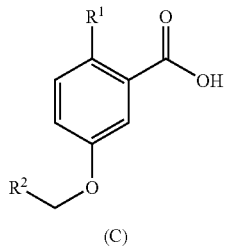

(C)

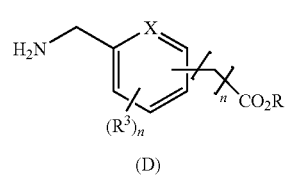

(D)

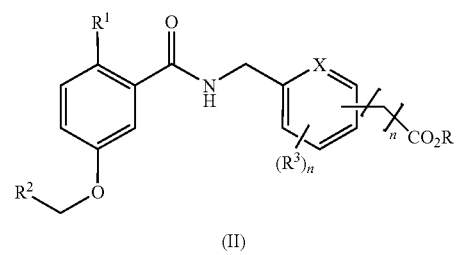

(II)

wherein, $R^1$, $R^2$, $R^3$, and X are as defined in formula (I), n is 0 or 1 and R represents a suitable alkyl ester protecting group, such as a methyl, ethyl or benzyl group.

Compounds of formula (II) may be obtained from compounds of formulae (C) and (D) using an amide coupling reagent such as dicyclohexylcarbodiimide or N-(3-dimethylaminopropyl)-N'-ethylcarbodiimide hydrochloride. The reaction is conveniently carried out in a solvent, such as dichloromethane, with or without a base, such as triethylamine, and at ambient or elevated temperature.

Alternatively, compounds of formula (II) may be obtained from compounds of formula (C) by a two-step procedure which entails first converting a compound of formula (C) to an acid chloride. This is conveniently achieved by treating a compound of formula (C) with a reagent such as thionyl chloride or oxalyl chloride at ambient or elevated temperature, and optionally in the presence of a sub-stoichiometric quantity of dimethylformamide. After removal of excess reagent by evaporation and, if necessary, azeotropic distillation with toluene, the crude acid chloride is treated with a compound of formula (D), typically in a solvent, such as dichloromethane, in the presence of a base, such as pyridine or triethylamine, and at ambient or elevated temperature.

Compounds of formula (D) are commercially available or are known in the literature and may be readily prepared from commercially available starting materials in accordance with methods known in the art. For example, methyl 4-(aminomethyl)benzoate hydrochloride is available from Sigma-Aldrich.

Compounds of formula (C) may be conveniently obtained by treating a compound of formula (B) with base, such as lithium hydroxide. The reaction may be conveniently carried out in a mixture of solvents, such as 1,4-dioxane/water, and at elevated temperature, for example 60° C.

Compounds of formula (B) may be obtained by treating a compound of formula (A) with an alkylating agent, such as an alkyl halide. The reaction is conveniently carried out in a solvent, such as dimethylformamide, in the presence of a base, such as potassium carbonate and at ambient or elevated temperature, for example 60° C.

Compounds of formula (A) are commercially available or may be prepared in accordance with methods known in the art. For example, 2-chloro-5-hydroxybenzoic acid is available from Apin Chemicals Ltd., UK.

Alternatively, compounds of formula (II) may be prepared according to Scheme 2 below:

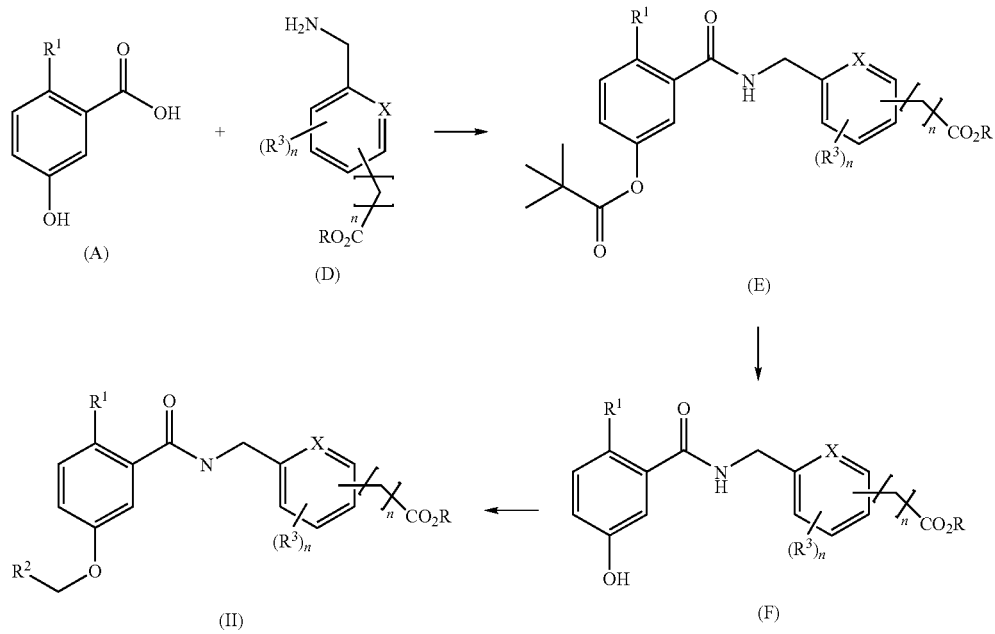

wherein, $R^1$, $R^2$, $R^3$, and X are as defined in formula (I), n is 0 or 1 and R represents a suitable alkyl ester protecting group, such as a methyl, ethyl or benzyl group Compounds of formula (II) may be obtained by treating a compound of formula (F) with an alkylating agent, such as an alkyl halide. The reaction is conveniently carried out in a solvent, such as dimethylformamide, in the presence of a base, such as potassium carbonate and at ambient or elevated temperature.

Alternatively, compounds of formula (II) may be obtained by treating a compound of formula (F) with an alcohol, in the presence of triphenylphosphine and diisopropylazodicarboxylate and in a solvent, such as tetrahydrofuran.

Compounds of formula (F) may be conveniently obtained by treating a compound of formula (E) with a base, such as sodium methoxide, in a solvent, such as methanol, and at ambient or elevated temperature.

Compounds of formula (E) may be obtained from compounds of formula (A) by a two-step procedure which entails first treating a compound of formula (A) with 2,2-dimethylpropanoyl chloride to form an intermediate acid anhydride. This is conveniently carried out in the presence of a base, such as triethylamine, in a solvent, such as dichloromethane, and at ambient or elevated temperature. The crude acid anhydride may then be converted to a compound of formula (E) without being isolated, by the addition of a compound of formula (D) to the reaction, along with further solvent and base.

In a further embodiment of the invention there is provided a process for preparing a compound of formula (I), where $R^4$ is tetrazolyl or a pharmaceutically acceptable derivative thereof, which process comprises converting a compound of formula (IIa),

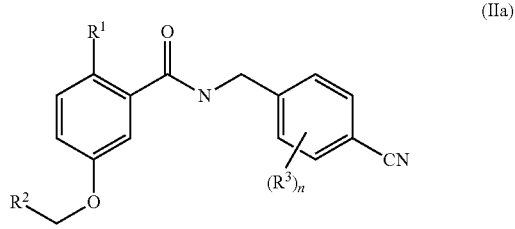

(IIa)

wherein, $R^1$, $R^2$, $R^3$ are as defined in formula (I), to a tetrazole derivative and optionally thereafter forming a pharmaceutically acceptable derivative of the compound so formed.

Suitable conditions for effecting this conversion include the use of a mixture of azidotrimethylsilane and trimethylaluminium in a solvent, such as toluene, and at elevated temperature, for example 80° C.

Compounds of formula (IIa) may be obtained from a compound of formula (C) and 4-(aminomethyl)benzonitrile using an amide coupling reagent such as dicyclohexylcarbodiimide or N-(3-dimethylaminopropyl)-N'-ethylcarbodiimide hydrochloride. The reaction is conveniently carried out in a solvent, such as dichloromethane, with or without a base, such as triethylamine, and at ambient or elevated temperature.

Alternatively, compounds of formula (IIa) may be obtained from a compound of formula (C) by a two-step procedure which entails first converting a compound of formula (C) to an acid chloride. This is conveniently achieved by treating a compound of formula (C) with a reagent such as thionyl chloride or oxalyl chloride at ambient or elevated temperature, and optionally in the presence of a sub-stoichiometric quantity of dimethylformamide. After removal of excess reagent by evaporation and, if necessary, azeotropic distillation with toluene, the crude acid chloride is treated with 4-(aminomethyl)benzonitrile, typically in a solvent, such as dichloromethane, in the presence of a base, such as pyridine or triethylamine, and at ambient or elevated temperature.

The following Descriptions and Examples illustrate the preparation of compounds of formula (I). Descriptions refer to intermediate compounds and Examples refer to compounds of formula (I). The starting material for the preparation of intermediates may not necessarily have been prepared from the batch referred to. The intermediates for the preparation of the examples may not necessarily have been prepared from the batch referred to.

INTERMEDIATE 1

(3-Chlorophenyl)methyl 2-chloro-5-{[(3-chlorophenyl)methyl]oxy}benzoate

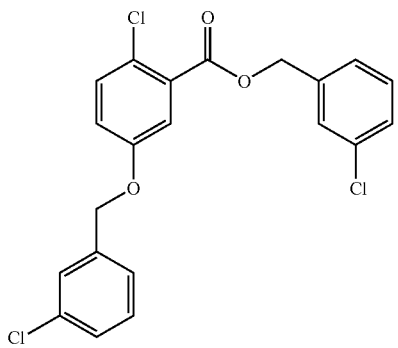

To a mixture of 2-chloro-5-hydroxybenzoic acid (500 mg, 2.9 mmol) in DMF (20 ml) were added potassium carbonate (1.0 g, 7.3 mmol, 2.5 eq) and 3-chlorobenzyl bromide (0.8 ml, 6.1 mmol, 2.1 eq). The mixture was heated at 60° C. for 2.5 hours. On cooling the mixture was diluted with ethyl acetate (300 ml) and washed with water (2×100 ml) then brine (70 ml). Organic layer dried and evaporated in vacuo. The residue was purified by column chromatography (Biotage SP4, 100 g silica column) eluting with 0-30% ethyl acetate in hexanes to afford the title compound as a clear oil (1.16 g). MS (ES+) m/z 421 [M+H]$^+$ ($C_{21}H_{15}{}^{35}Cl_2O_3$). $^1$H-NMR (400 MHz, $d_6$-DMSO) δ 5.19 (2H,s), 5.35 (2H,s), 7.26 (1H,dd, J 8.8, J 3.2), 7.40-7.56 (10H,m).

INTERMEDIATE 2

2-Chloro-5-{[(3-chlorophenyl)methyl]oxy}benzoic acid

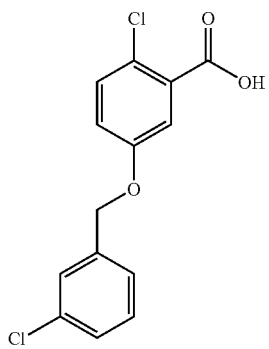

A solution of (3-chlorophenyl)methyl 2-chloro-5-{[(3-chlorophenyl)methyl]oxy}benzoate (970 mg, 2.3 mmol) in dioxane (30 ml) and water (15 ml) was treated with lithium hydroxide (monohydrate) (145 mg, 3.5 mmol, 1.5 eq). The resulting mixture was stirred at room temperature for 2 hours. The solvent was then evaporated in vacuo, the residue take up into water (50 ml) and washed with ether (100 ml). The aqueous layer was then acidified with 2M HCl the extracted with ether (2×150 ml). Organic layers combined, washed with brine, dried and evaporated in vacuo to afford the title product as a white solid (600 mg). MS (ES−) m/z 295 [M−H]$^-$ ($C_{14}H_{10}{}^{35}Cl_2O_3$). $^1$H-NMR (400 MHz, $d_6$-DMSO) δ 5.17 (2H,s), 7.17-7.20 (1H, m), 7.38-7.53 (6H,m), 13.4 (1H, s).

Intermediates 3 to 17 were obtained from the appropriate substituted 5-hydroxybenzoic acid by a similar two-step method (alkylation followed by ester hydrolysis) to that used for intermediate 2, with any differences from the described procedures noted in the following table:

| Int No | | Comments and MS |
|---|---|---|
| 3 | (structure) | alkylation: 2.0 eq alkylating agent, 2.0 eq $K_2CO_3$; heated 70° C. for 2 hours, then room temp. overnight, then 80° C. for 6 hours. Crude product not purified further. hydrolysis: stirred at room temperature overnight; further LiOH·$H_2O$ (1.5 eq) added; stirred at room temperature overnight. MS [$C_{15}H_{13}{}^{35}ClO_3$ M − H]$^-$ 275 |

| Int No | Structure | Comments and MS |
|---|---|---|
| 4 | 2-methyl-5-(benzyloxy)benzoic acid | alkylation: 2.0 eq alkylating agent, 2.0 eq K$_2$CO$_3$; heated 70° C. for 2 hours, then room temp. overnight, then 80° C. for 6 hours. Crude product not purified further.<br>hydrolysis: stirred at room temperature overnight; further LiOH•H$_2$O (1.5 eq) added; stirred at room temperature overnight.<br>MS [C$_{15}$H$_{14}$O$_3$ M − H]$^-$ 241 |
| 5 | 6-chloro-2-fluoro-3-(3-chlorobenzyloxy)benzoic acid | alkylation: 2.1 eq alkylating agent, 2.4 eq K$_2$CO$_3$.<br>hydrolysis: heated at 50° C. overnoght; acidified with 5N HCl, precipitated solid collected to furnish product.<br>MS [C$_{14}$H$_9$$^{35}$Cl$_2$FO$_3$ M − H]$^-$ 313 |
| 6 | 2-fluoro-5-(benzyloxy)benzoic acid | alkylation: 2.2 eq alkylating agent, 2.5 eq K$_2$CO$_3$; heated 80° C. for 2 hours, then room temp. over weekend. Crude product not purified further.<br>hydrolysis work up: solvent evaporated, residue partitioned 2N HCl and Et$_2$O. Ether layer evaporated, residue taken up in 2N NaOH, washed EtOAc, aqueous layer acidified with 2N HCl then extracted with Et$_2$O as decribed.<br>MS [C$_{14}$H$_{11}$FO$_3$ M − H]$^-$ 245 |
| 7 | 2-fluoro-5-(3-chlorobenzyloxy)benzoic acid | alkylation: 2.2 eq alkylating agent, 2.5 eq K$_2$CO$_3$; heated 80° C. for 2 hours, then room temp. over weekend. Crude product not purified further.<br>hydrolysis work up: solvent evaporated, residue partitioned 2N HCl and Et$_2$O. Ether layer evaporated, residue taken up in 2N NaOH, washed EtOAc, aqueous layer acidified with 2N HCl then extracted with Et$_2$O as decribed.<br>MS [C$_{14}$H$_{10}$$^{35}$ClFO$_3$ M − H]$^-$ 279 |
| 8 | 2-chloro-5-(3-fluorobenzyloxy)benzoic acid | alkylation: stirred at room temperature for 67 h. Reaction mixture diluted EtOAc, filtered, washed with water then brine. Crude product not purified further.<br>hydrolysis: stirred 16 hours at room temperature.<br>MS [C$_{14}$H$_{10}$$^{35}$ClFO$_3$ M − H]$^-$ 279 |
| 9 | 2-chloro-5-(3-methylbenzyloxy)benzoic acid | alkylation: stirred at room temperature for 67 h. Reaction mixture diluted EtOAc, filtered, washed with water then brine. Crude product not purified further.<br>hydrolysis: stirred 16 hours at room temperature.<br>MS [C$_{15}$H$_{13}$$^{35}$ClO$_3$ M − H]$^-$ 275 |
| 10 | 2-chloro-5-(4-chlorobenzyloxy)benzoic acid | alkylation: Heated at 50° C. for 20 hours. Reaction mixture diluted EtOAc, filtered, washed with water then brine. Crude product not purified further.<br>hydrolysis: heated at 65° C. for 6 hours then stirred at room temperature for 16 hours.<br>MS [C$_{14}$H$_{10}$$^{35}$Cl$_2$O$_3$ M − H]$^-$ 295 |

| Int No | | Comments and MS |
|---|---|---|
| 11 | 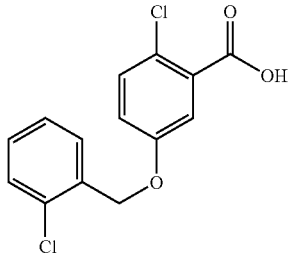 | alkylation: Heated at 50° C. for 20 hours. Reaction mixture diluted EtOAc, filtered, washed with water then brine. Crude product not purified further.<br>hydrolysis: heated at 65° C. for 6 hours then stirred at room temperature for 16 hours.<br>MS [$C_{14}H_{10}{}^{35}Cl_2O_3$ M − H]⁻ 295 |
| 12 | 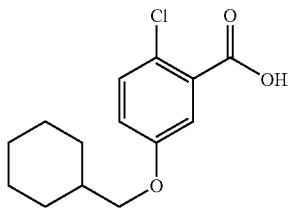 | alkylation: 2.2 eq alkylating agent, 2.5 eq $K_2CO_3$; heated 80° C. for 3 hours, further alkylating agent added (2.2 eq), heated 80° C. for 1 hour. Crude product not purified further.<br>hydrolysis: stirred at room temperature overnight; worked up using EtOAc in place of $Et_2O$.<br>MS [$C_{14}H_{17}{}^{35}ClO_3$ M − H]⁻ 267 |
| 13 | 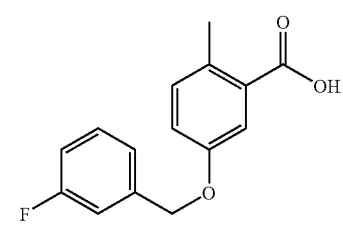 | alkylation: stirred at room temperature for 24 hours, further alkylating agent (0.25 eq) added, heated at 65° C. for 24 hours; reaction mixture diluted EtOAc, filtered, washed with water then brine. Crude product not purified further.<br>hydrolysis: stirred at room temperature for 6 hours, heated at 65° C. for 2 hours, then stirred at room temperature for 16 hours.<br>MS [$C_{15}H_{13}FO_3$ M − H]⁻ 259 |
| 14 | 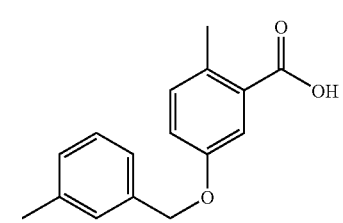 | alkylation: stirred at room temperature for 24 hours, further alkylating agent (0.25 eq) added, heated at 65° C. for 24 hours; reaction mixture diluted EtOAc, filtered, washed with water then brine. Crude product not purified further.<br>hydrolysis: stirred at room temperature for 6 hours, heated at 65° C. for 2 hours, then stirred at room temperature for 16 hours.<br>MS [$C_{15}H_{13}FO_3$ M − H]⁻ 259 |
| 15 | 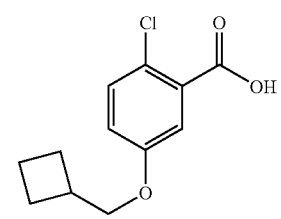 | alkylation: 2.2 eq. alkylating agent, heated 80° C. for 3 hours. Further 2.2 eq. alkylating agent, heated 80° C. for 1 hour. Crude product not purified further.<br>hydrolysis: stirred at room temperature for 18 hours.<br>MS [$C_{12}H_{13}{}^{35}ClO_3$ M + H]⁺ 241 |
| 16 | 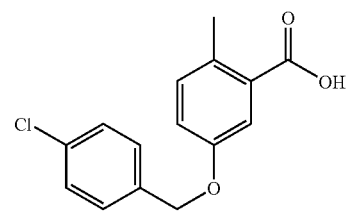 | alkylation: Heated at 50° C. for 20 hours. Reaction mixture diluted EtOAc, filtered, washed with water then brine. Crude product not purified further.<br>hydrolysis: heated at 65° C. for 6 hours then stirred at room temperature for 16 hours.<br>MS [$C_{15}H_{13}{}^{35}ClO_3$ M − H]⁻ 275 |

-continued

| Int No | | Comments and MS |
|---|---|---|
| 17 | 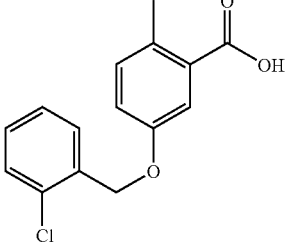 | alkylation: Heated at 50° C. for 20 hours. Reaction mixture diluted EtOAc, filtered, washed with water then brine. Crude product not purified further. hydrolysis: heated at 65° C. for 6 hours then stirred at room temperature for 16 hours. MS [$C_{15}H_{13}{}^{35}ClO_3$ M − H]⁻ 275 |

INTERMEDIATE 18

Methyl 4-({[(2-chloro-5-{[(3-chlorophenyl)methyl]oxy}phenyl)carbonyl]amino}methyl)benzoate

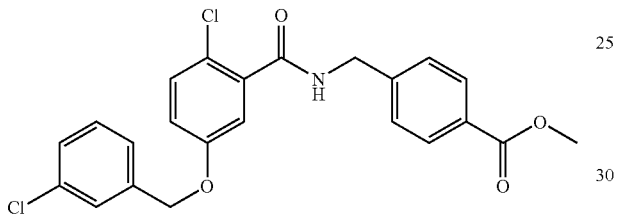

A solution of 2-chloro-5-{[(3-chlorophenyl)methyl]oxy}benzoic acid (250 mg, 0.84 mmol) and N-[3-(dimethylamino)propyl]-N'-ethylcarbodiimide hydrochloride (250 mg, 1.3 mmol) in DCM (3 ml) was stirred at room temperature for 30 min. A solution of methyl 4-(aminomethyl)benzoate hydrochloride (262 mg, 1.3 mmol) in DCM (2 ml) was added followed by N-ethyl-N-(1-methylethyl)-2-propanamine (220 ul, 1.3 mmol). The mixture was heated at 40° C. overnight. The mixture was then diluted with methanol and purified by SCX cartridge eluting with methanol. The fractions were combined and evaporated to give the title compound as a white solid. MS (ES+) m/z 444 [M+H]⁻ ($C_{23}H_{19}{}^{35}Cl_2NO_4$). ¹H-NMR (400 MHz, $d_6$-DMSO) δ 3.85 (3H, s), 4.51 (2H, d, J 4), 5.17 (2H, s), 7.12 (2H, d, J 8), 7.42-7.49 (7H, m), 7.95 (2H, d, J 8), 9.06 (1H, s).

The following intermediate 19 was prepared in a similar manner to intermediate 18 above:

INTERMEDIATE 20

Ethyl [3-(aminomethyl)phenyl]acetate hydrochloride

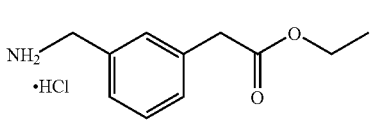

A mixture of (3-cyanophenyl)acetic acid (3 g, 18.6 mmol), 10% palladium on charcoal (300 mgs) and conc. hydrochloric acid (3 eqs, 4.6 mls, 55.8 mmol) in ethanol (100 mls) was subject to an atmosphere of hydrogenation overnight. The resulting mixture was filtered through hyflo and the catalyst washed thoroughly with ethanol. The solvent was then evaporated in vacuo to give a crunchy white solid. This was triturated with ether, filtered off and dried to afford a white solid (2.76 g). ¹H-NMR (400 MHz, $d_4$-MeOH) δ 1.24 (3H,t, J 8.0), 3.69 (2H,s), 4.11 (2H,s), 4.15 (2H,q, J 13.2 6.0), 7.17-7.20 (1H, m), 7.34-7.44 (4H, m).

| Int No | | Comments |
|---|---|---|
| 19 | 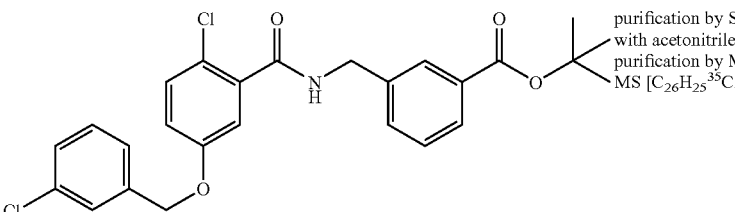 | purification by SCX done eluting with acetonitrile and followed by purification by MDAP MS [$C_{26}H_{25}{}^{35}Cl_2NO_4$ M + H]⁺ 486 |

INTERMEDIATE 21

Methyl 4-({[(5-{[(3-chlorophenyl)methyl]oxy}-2-fluorophenyl)carbonyl]amino}methyl)benzoate

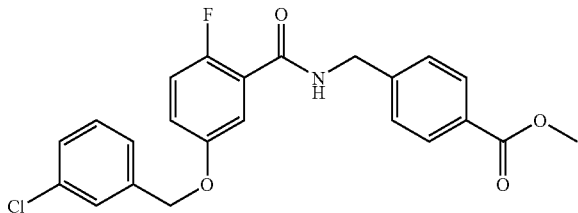

A solution of 5-{[(3-chlorophenyl)methyl]oxy}-2-fluorobenzoic acid (343 mg, 1.22 mmol) in dichloromethane (5 ml) was treated with oxalyl chloride (1.5 eqs, 160 ul, 1.83 mmol) and DMF (1 drop). Effervescence was observed and the mixture was stirred at room temperature for 1 hour. The solvent was then evaporated in vacuo and azeotroped with toluene. A portion of the resulting solid (122 mgs, 0.41 mmol) was dissolved in dichloromethane (5 ml) and treated with triethylamine (2.5 eqs, 142 ul, 1.02 mmol) and methyl 4-(aminomethyl)benzoate hydrochloride (1.5 eqs, 124 mg, 0.61 mmol). The mixture was stirred at room temperature for 18 hours. The mixture was then diluted with methanol and purified by SCX cartridge eluting with methanol. Fractions combined and evaporated to give the title compound as a white solid (227 mg). MS (ES+) m/z 428 [M+H]$^+$ ($C_{23}H_{19}{}^{35}ClFNO_4$).

The following intermediates 22 to 43 were prepared by a similar two-step method to methyl 4-({[(5-{[(3-chlorophenyl)methyl]oxy}-2-fluorophenyl)carbonyl]amino}methyl)benzoate (intermediate 21) from the appropriate starting materials with any differences from the described procedure noted in the following table:

| Int No | Structure | Comments and MS |
|---|---|---|
| 22 | | Acid chloride formation: mixture stirred for 30 min at room temperature.<br>Amide formation: mixture stirred at room temp for 2 hours, then diluted with DCM, washed with NaHCO3 and brine, dried over MgSO4 and evaporated. Residue purified by MDAP.<br>MS [$C_{22}H_{18}{}^{35}Cl_2N_2O_4$ M + H]$^+$ 445 |
| 23 | | Acid chloride formation:- room temp. 2 hours.<br>Amide formation:- Attempted purification by MDAP. Not soluble. Product filtered off from MDAP solution and dried. No further purification.<br>MS [$C_{24}H_{22}{}^{35}ClNO_4$ M + H]$^+$ 424 |
| 24 | | Acid chloride formation: mixture stirred for 30 min at room temperature.<br>Amide formation: mixture stirred at room temp for 2 hours.<br>MS [$C_{23}H_{18}{}^{35}Cl_2FNO_4$ M + H]$^+$ 462 |
| 25 | | Acid chloride formation: mixture stirred for 30 min at room temperature.<br>Amide formation: mixture stirred at room temp for 2 hours. After SCX further purification was required so the residue was purified by column chromatography (Biotage SP4) eluting with 0-40% EtOAc/Hex.<br>MS [$C_{24}H_{21}{}^{35}Cl_2NO_4$ M + H]$^+$ 458 |

-continued

| Int No | | Comments and MS |
|---|---|---|
| 26 | 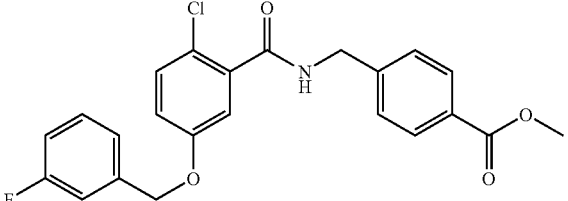 | Acid chloride formation: mixture stirred for 30 min at room temperature.<br>Amide formation: mixture stirred at room temp for 2 hours.<br>MS $[C_{23}H_{19}{}^{35}ClFNO_4 \text{ M} + \text{H}]^+$ 428 |
| 27 | 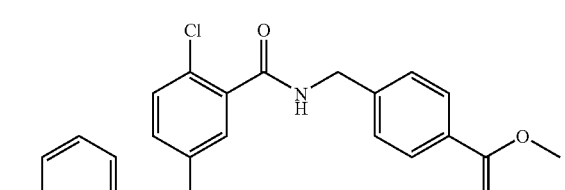 | Acid chloride formation: mixture stirred for 30 min at room temperature.<br>Amide formation: mixture stirred at room temp for 2 hours.<br>MS $[C_{24}H_{22}{}^{35}ClNO_4 \text{ M} + \text{H}]^+$ 424 |
| 28 | 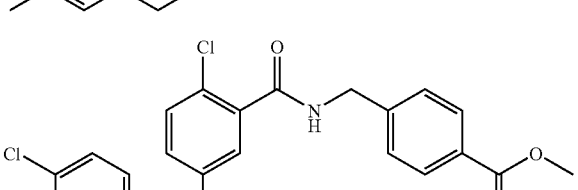 | Same as procedure for intermediate 21.<br>MS $[C_{23}H_{19}{}^{35}Cl_2NO_4 \text{ M} + \text{H}]^+$ 444 |
| 29 | 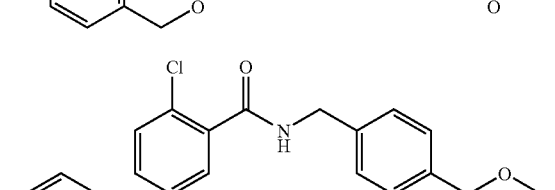 | Same as procedure for intermediate 21.<br>MS $[C_{23}H_{19}{}^{35}Cl_2NO_4 \text{ M} + \text{H}]^+$ 444 |
| 30 | 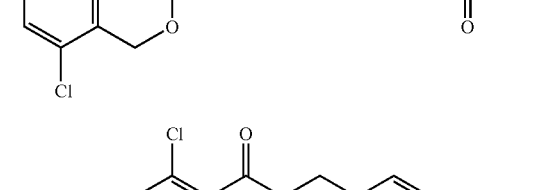 | Same as procedure for intermediate 21.<br>MS $[C_{23}H_{26}{}^{35}ClNO_4 \text{ M} + \text{H}]^+$ 416 |
| 31 | 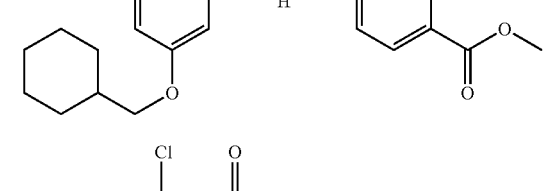 | Same as procedure for intermediate 21.<br>MS $[C_{21}H_{22}{}^{35}ClNO_4 \text{ M} + \text{H}]^+$ 388 |
| 32 | 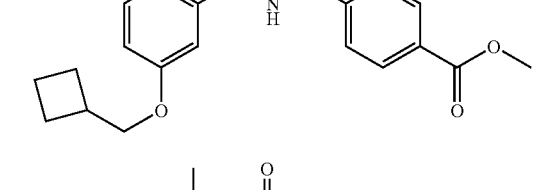 | Acid chloride formation: mixture stirred for 30 min at room temperature.<br>Amide formation: mixture stirred at room temp for 2 hours.<br>MS $[C_{24}H_{22}FNO_4 \text{ M} + \text{H}]^+$ 408 |

| Int No | | Comments and MS |
|---|---|---|
| 33 | 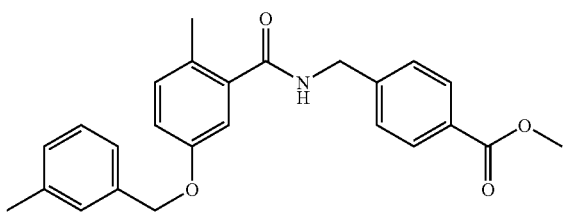 | Acid chloride formation: mixture stirred for 30 min at room temperature.<br>Amide formation: mixture stirred at room temp for 2 hours then evaporated in vacuo and triturated with methanol.<br>MS [$C_{25}H_{25}NO_4$ M + H]$^+$ 404 |
| 34 | 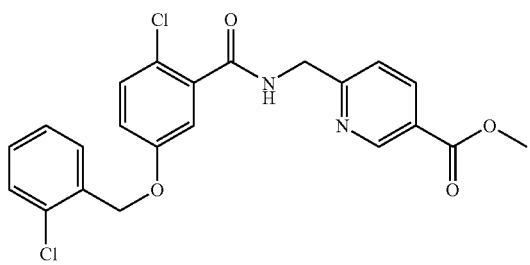 | Acid chloride formation: mixture stirred for 30 min at room temperature.<br>Amide formation: after stirring at room temp for 18 hours, mixture was diluted with DCM, washed with NaHCO3 and brine, dried over MgSO4 and evaporated. Residue purified by MDAP.<br>MS [$C_{22}H_{18}{}^{35}Cl_2N_2O_4$ M + H]$^+$ 445 |
| 35 | 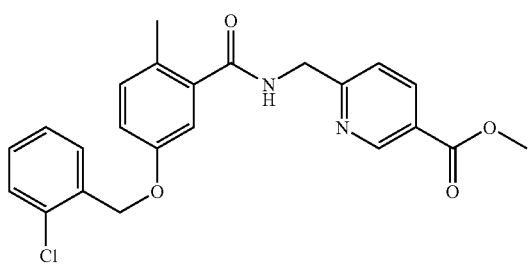 | Amide formation:- product eluted from the SCX cartridge using 2M ammonia in methanol.<br>MS [$C_{23}H_{21}{}^{35}ClN_2O_4$ M + H]$^+$ 425 |
| 36 | 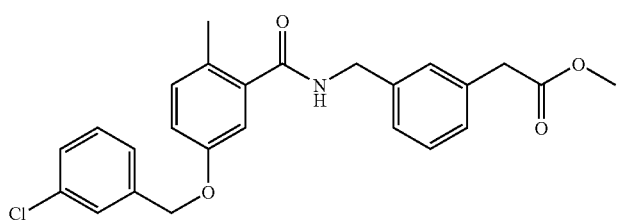 | Acid chloride formation:- room temp. 2 hours.<br>Amide formation:- stirred at room temp. over the weekend. Acetonitrile used for SCX.<br>MS [$C_{26}H_{26}{}^{35}ClNO_4$ M + H]$^+$ 452 |
| 37 | 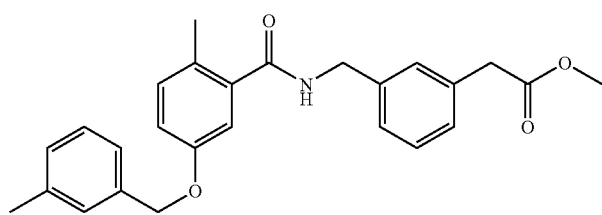<br>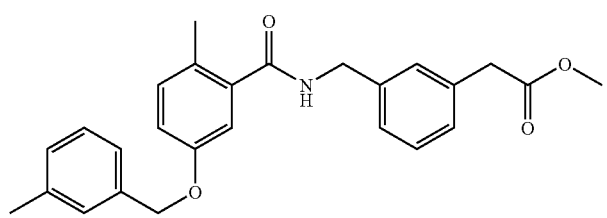 | Acid chloride formation: mixture stirred for 30 min at room temperature.<br>Amide formation: for SCX acetonitrile was used as eluent followed by 2M NH$_4$OH in methanol, so mixture of Me ester and Et ester formed. Mixture purified by MDAP collecting both Me and Et ester as a mixture<br>MS Ethyl ester: [$C_{27}H_{29}NO_4$ M + H]$^+$ 432<br>Methyl ester: [$C_{26}H_{27}NO_4$ M + H]$^+$ 418 |

-continued

| Int No | | Comments and MS |
|---|---|---|
| 38 | 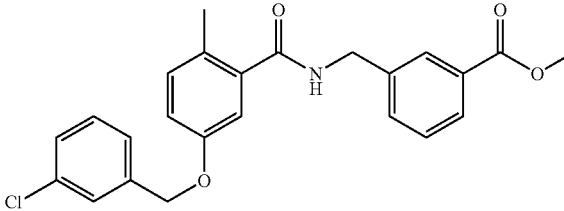 | Acid chloride formation:- room temp. 2 hours.<br>Amide formation:- 1.5 eqs. triethylamine.<br>Acetonitrile used for SCX.<br>MS $[C_{23}H_{20}{}^{35}ClNO_4\ M + H—CH_2C(CH_3)]^+$ 410 |
| 39 | 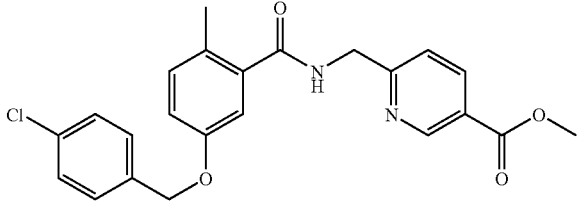 | Acid chloride formation:- room temp. 2 hours.<br>Amide formation:- reaction mixture evaporated in vacuo. No further purification.<br>MS $[C_{22}H_{18}{}^{35}ClN_2O_4\ M + H]^+$ 425 |
| 40 | 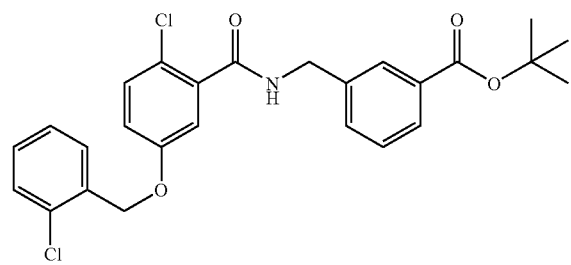 | Acid chloride formation: mixture stirred for 30 min at room temperature.<br>Amide formation: Acetonitrile used for SCX.<br>MS $[C_{26}H_{25}{}^{35}Cl_2NO_4\ M + H]^+$ 486 |
| 41 | 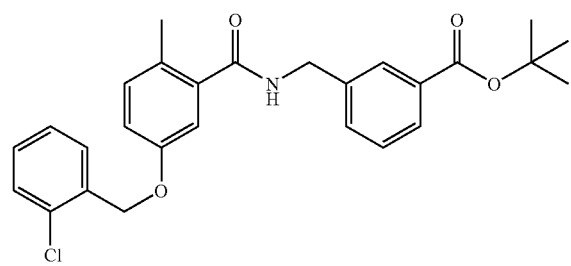 | Acid chloride formation: mixture stirred for 30 min at room temperature.<br>Amide formation: Acetonitrile used for SCX.<br>MS $[C_{27}H_{28}{}^{35}ClNO_4\ M + H]^+$ 466 |
| 42 | 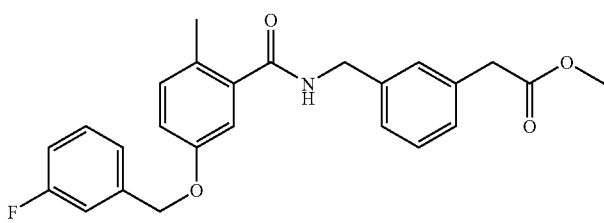 | Acid chloride formation: mixture stirred for 30 min at room temperature.<br>Amide formation: for SCX acetonitrile was used as eluent followed by 2 M NH4OH in methanol, mixture of Me ester and Et ester formed.<br>MS Ethyl ester: $[C_{26}H_{28}FNO_4\ M + H]^+$ 436<br>Methyl ester: $[C_{25}H_{26}FNO_4\ M + H]^+$ 422 |

-continued

| Int No | | Comments and MS |
|---|---|---|
| 43 | 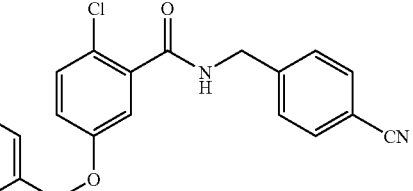 | Acid chloride formation: mixture stirred for 45 min at room temperature. Amide formation: 1.4 eq amine, 3.3 eq triethylamine, stirred 18 hours at room temperature, reaction diluted with DCM, washed with saturated aqueous NaHCO$_3$, layers separated, organic concentrated to give crude product. Purified by MDAP. MS [C$_{22}$H$_{16}$$^{35}$Cl$_2$N$_2$O$_2$ M + H]$^+$ 411 |

INTERMEDIATE 44

Methyl 4-{[({2-chloro-5-[(2,2-dimethylpropanoyl)oxy]phenyl}carbonyl)amino]methyl}benzoate

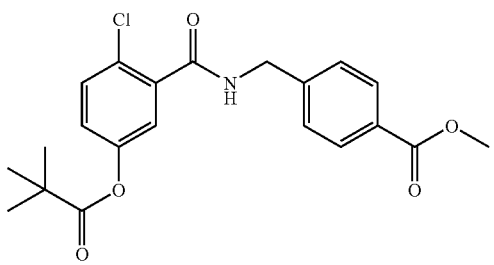

A solution of 2-chloro-5-hydroxybenzoic acid (1.0 g, 5.8 mmol) in DCM (10 ml) was treated with triethylamine (2.5 eq, 2.0 ml, 14.5 mmol) and 2,2-dimethylpropanoyl chloride (2.0 eq, 1.43 ml, 11.6 mmol). Mixture stirred at room temperature for 2 hours. A solution of methyl 4-(aminomethyl)benzoate hydrochloride (1.5 eq, 1.75 g, 8.7 mmol) and triethylamine (2.0 eq, 1.6 ml, 11.6 mmol) in DCM (10 ml) was then added and the mixture stirred at room temperature for another 2 hours. The mixture was diluted with DCM (300 ml) and aqueous sodium bicarbonate (100 ml), layers separated and aqueous layer extracted again with DCM (200 ml). Organic layers combined, washed with brine, dried over magnesium sulphate and evaporated. Residue purified by column chromatography (Biotage SP4) eluting with 0-30% EtOAc in Hex to give the title compound as a white solid. MS (ES+) m/z 404 [M+H]$^+$ (C$_{21}$H$_{22}$$^{35}$ClNO$_5$). $^1$H-NMR (400 MHz, d$_6$-DMSO) δ 1.30 (9H, s), 3.85 (3H, s), 4.51 (2H, d, J 6), 7.24 (1H, dd, J 8.8, J 2.8), 7.29 (1H, d, J 2.8), 7.51 (2H, d, J 8.8), 7.56 (2H, d, J 8.4), 7.95 (2H, m).

INTERMEDIATE 45

Methyl 4-({[(2-chloro-5-hydroxyphenyl)carbonyl]amino}methyl)benzoate

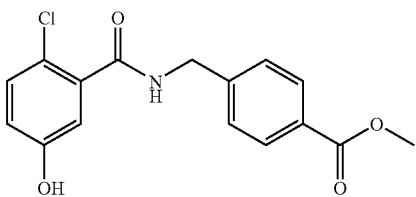

A solution of methyl 4-{[({2-chloro-5-[(2,2-dimethylpropanoyl)oxy]phenyl}carbonyl)amino]methyl}benzoate (590 mg, 1.46 mmol) and sodium methoxide (1.2 eq, 95 mg, 1.76 mmol) in methanol (10 ml) was heated at 65° C. overnight. On cooling the solvent was evaporated in vacuo to give the title compound as a white solid. MS (ES+) m/z 320 [M+H]$^+$ (C$_{16}$H$_{14}$$^{35}$ClNO$_4$). $^1$H-NMR (400 MHz, d$_6$-DMSO) δ 3.84 (3H, s), 4.45 (2H, d, J 6), 6.55 (2H, m), 6.99 (1H, d, J 8.8), 7.46 (2H, d, J 8.4), 7.92 (2H, m), 8.82 (1H, t).

INTERMEDIATE 46

Methyl 4-[({[2-chloro-5-({[3-(methyloxy)phenyl]methyl}oxy)phenyl]carbonyl}amino)methyl]benzoate

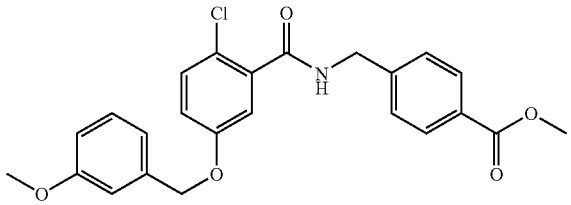

A solution of methyl 4-({[(2-chloro-5-hydroxyphenyl)carbonyl]amino}methyl)benzoate (95 mg, 0.3 mol), potassium carbonate (2 eq, 83 mg, 0.6 mmol) and 1-(bromomethyl)-3-(methyloxy)benzene (1.2 eq, 50 ul, 0.36 mmol) in DMF (2 ml) was stirred at room temperature for 2 hours. The mixture was then diluted with ethyl acetate (100 ml) and H$_2$O (80 ml). Layers separated, organic layer washed with brine (80 ml) then dried and evaporated in vacuo. Residue purified by column chromatography (Biotage SP4) eluting with 0-40% ethylacetate in hexanes to give the title compound as a clear oil. MS (ES+) m/z 440 [M+H]$^+$ (C$_{24}$H$_{22}$$^{35}$ClNO$_5$). $^1$H-NMR (400 MHz, d$_6$-DMSO) δ 3.76 (3H, s), 3.85 (3H, s), 4.51 (2H, d, J 6), 5.12 (2H, s), 6.89-7.96 (11H, m), 7.46 (2H, d, J 8.4), 7.92 (2H, m), 9.05 (1H, J 6).

The following intermediates 47 and 48 were prepared by a similar two-step method to methyl 4-[({[2-chloro-5-({[3-(methyloxy)phenyl]methyl}oxy)phenyl]carbonyl}amino)methyl]benzoate (intermediate 46) from the appropriate starting materials:

| Int No | | MS |
|---|---|---|
| 47 | | $[C_{23}H_{18}{}^{35}ClF_2NO_4\ M+H]^+$ 446 |
| 48 | | $[C_{24}H_{19}{}^{35}ClF_3NO_4\ M+H]^+$ 478 |

INTERMEDIATE 49

Methyl 4-({[(2-chloro-5-{[(2-methyl-3-pyridinyl)methyl]oxy}phenyl)carbonyl]amino}methyl)benzoate

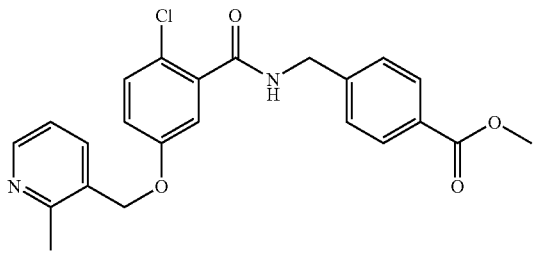

A solution of methyl 4-({[(2-chloro-5-hydroxyphenyl)carbonyl]amino}methyl)benzoate (100 mg, 0.31 mmol) in THF (5 ml) was treated with triphenylphosphine (1.2 eq, 98 mg, 0.37 mmol), (2-methyl-3-pyridinyl)methanol (38 mg, 0.31 mmol) and diisopropylazodicarboxylate (1.2 eq, 110 ul, 0.56 mmol) and stirred at room temperature for 4 hours. Mixture diluted with methanol and purified by SCX cartridge eluting with methanol first then 2M ammonia in methanol. Basic fractions combined and evaporated to give the title compound as an off-white solid. MS (ES+) m/z 425 [M+H]$^+$ ($C_{23}H_{21}{}^{35}ClN_2O_4$). $^1$H-NMR (400 MHz, d$_6$-DMSO) δ 3.85 (3H, s), 4.51 (2H, d, J 6), 5.18 (2H, s), 7.10-7.96 (9H, m), 8.42 (1H, dd, J 1.6, J 4.8), 9.07 (1H, t, J 6).

The following intermediate 50 was prepared in a similar manner to intermediate 49 above:

| Int No | | Comments and MS |
|---|---|---|
| 50 | | same as intermediate 53, followed by failed attempt to dissolve in 1:1 MeOH/DMSO for MDAP purification, so mixture was purified again by SCX (as described in method) MS [$C_{23}H_{21}{}^{35}ClN_2O_4\ M+H$]$^+$ 424 |

EXAMPLE 1

4-({[(2-chloro-5-{[(2-chlorophenyl)methyl]oxy}phenyl)carbonyl]amino}methyl)benzoic acid

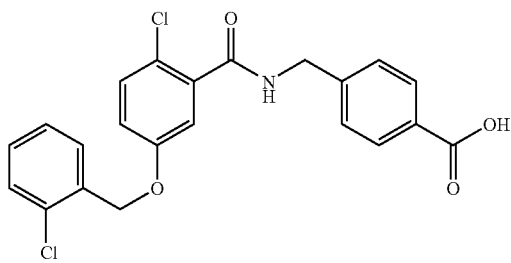

A solution of methyl 4-({[(2-chloro-5-{[(2-chlorophenyl)methyl]oxy}phenyl)carbonyl]amino}methyl)benzoate (113 mg, 0.25 mmol) in acetic acid (10 ml) and 2M HCl (10 ml) was heated at 90° C. for 6 hours. Heating continued at 90° C. overnight. A solid crashed out on cooling. The resulting solid was filtered, washed with water and dried to give the title compound as a white solid (67 mg). MS (ES+) m/z 430 [M+H]$^+$ (C22H$_{17}$$^{35}$Cl$_2$NO$_4$). $^1$H-NMR (400 MHz, d$_6$-DMSO) δ 4.51 (2H,d, J 6.0), 5.20 (2H,s), 7.11-7.16 (2H, m), 7.37-7.54 (6H,m), 7.59-7.62 (1H,m), 7.91-7.94 (2H,m), 9.10 (1H,t, J 6.0), 12.89 (1H, s).

The following examples 2 to 19 were prepared by a similar two-step method to 4-({[(2-chloro-5-{[(2-chlorophenyl)methyl]oxy}phenyl)carbonyl]amino}methyl)benzoic acid (example 1) from the appropriate intermediate with any differences from the described procedure noted in the following table:

| Ex No | | Comments and MS |
|---|---|---|
| 2 | | After heating overnight at 90° C., 5M HCl (3 ml) added and mixture heated at 90° C. over weekend. 3 ml dioxane added and mixture heated overnight. On cooling water was added and mixture filtered, attempt to dissolve solid in MeCN/DMSO 1:1 failed so solid was filtered and triturated with ether, then methanol then DCM to give title compound. MS [C$_{22}$H$_{17}$$^{35}$Cl$_2$NO$_4$ M + H]$^+$ 430 |
| 3 | | 2 ml dioxane added then mixture heated at 90° C. over weekend. Solvent evaporated in vacuo, residue purified by MDAP. MS [C$_{22}$H$_{17}$$^{35}$Cl$_2$NO$_4$ M + H]$^+$ 430 |
| 4 | | Heated at 90° C. for 2 hours. 3 ml dioxane added and mixture heated at 90° C. overnight. Solvent evaporated in vacuo, residue purified by MDAP. MS [C$_{21}$H$_{16}$$^{35}$Cl$_2$N$_2$O$_4$ M + H]$^+$ 431 |
| 5 | | Heated at 90° C. for 5 hours. Heating continued for a further 3 x 2 hours. Stirred at room temp for ~2 weeks. MS [C$_{23}$H$_{20}$$^{35}$ClNO$_4$ M + H]$^+$ 410 |

-continued

| Ex No | | Comments and MS |
|---|---|---|
| 6 | 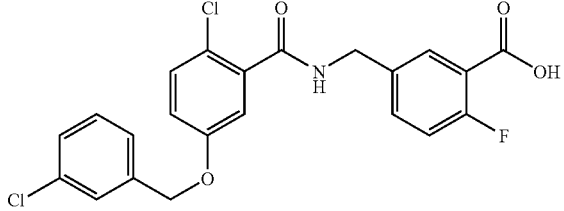 | Further purification by MDAP required.<br>MS [$C_{22}H_{16}{}^{35}Cl_2FNO_4$ M + H]$^+$ 448 |
| 7 | 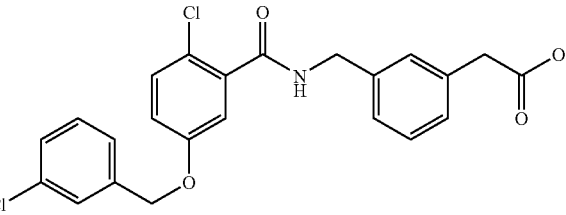 | Heated at 90° C. for 2 hours<br>MS [$C_{23}H_{19}{}^{35}Cl_2NO_4$ M + H]$^+$ 444 |
| 8 | 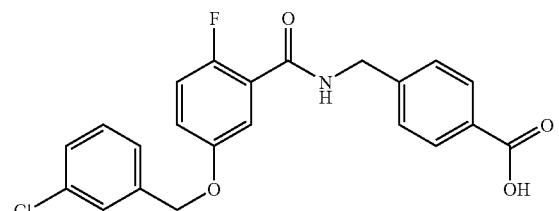 | Heated at 90° C. for 2 + 3 + 6 hours. Solid crashed out on cooling. Solid purified by MDAP.<br>MS [$C_{22}H_{17}{}^{35}ClFNO_4$ M + H]$^+$ 414 |
| 9 | 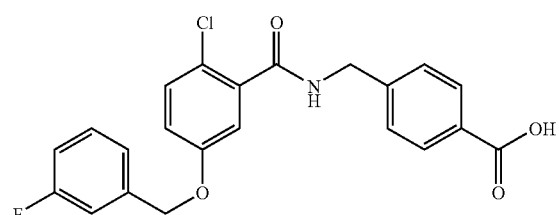 | Heated at 90° C. for 2 hours. 3 ml dioxane added and mixture heated at 90° C. overnight. Water added, mixture filtered to give a solid which was triturated with DCM to give final product.<br>MS [$C_{22}H_{17}{}^{35}ClFNO_4$ M + H]$^+$ 414 |
| 10 | 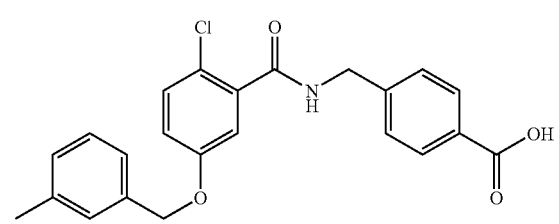 | Heated at 90° C. for 2 hours. 3 ml dioxane added and mixture heated at 90° C. overnight. Solvent evaporated in vacuo, residue purified by MDAP.<br>MS [$C_{23}H_{20}{}^{35}ClNO_4$ M + H]$^+$ 410 |
| 11 | 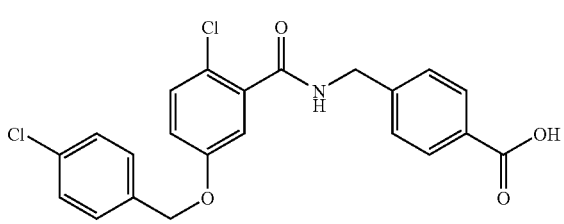 | Heated at 90° C. for 2 hours. Heating continued overnight.<br>MS [$C_{22}H_{17}{}^{35}Cl_2NO_4$ M + H]$^+$ 430 |
| 12 | 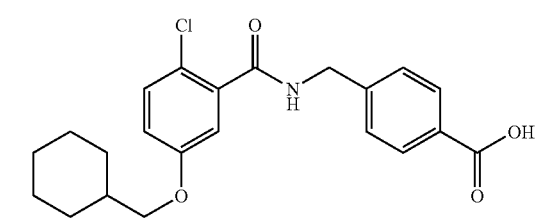 | Heated at 90° C. overnight.<br>MS [$C_{22}H_{24}{}^{35}ClNO_4$ M + H]$^+$ 402 |

| Ex No | | Comments and MS |
|---|---|---|
| 13 | 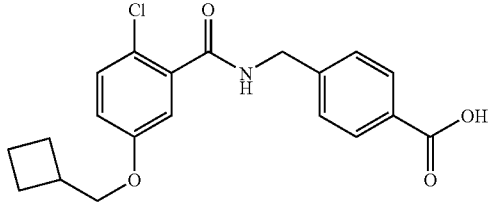 | Heated at 90° C. overnight.<br>MS $[C_{20}H_{20}{}^{35}ClNO_4 M + H]^+$ 374 |
| 14 | 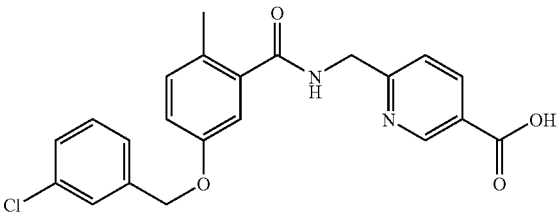 | Heated at 90° C. for 2 hours. Stirred at room temp. overnight. Heating continued for 6 + 6 hours. Reaction mixture evaporated in vacuo and then purified by MDAP.<br>MS $[C_{22}H_{19}{}^{35}ClN_2O_4 M + H]^+$ 411 |
| 15 | 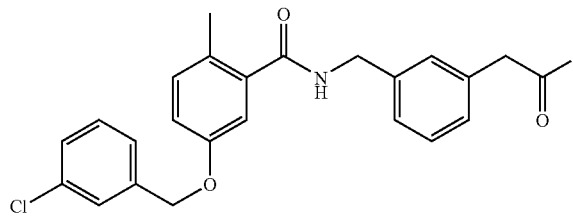 | Heated at 90° C. for 2 hours. Allowed to cool, diluted with water. Solid that crashed out was filtered off and dried.<br>MS $[C_{24}H_{22}{}^{35}ClNO_4 M + H]^+$ 424 |
| 16 | 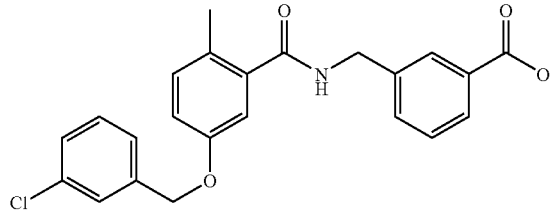 | Heated at 90° C. for 2 hours. Stirred at room temp overnight, diluted with water. Solid that crashed out was filtered off and dried (not clean). Tried to MDAP but not soluble in DMSO/MeOH. White solid filtered off (aniline). A solid crashed out of the filtrate. This was filtered off (not clean). However, now soluble for MDAP purification.<br>MS $[C_{23}H_{20}{}^{35}ClNO_4 M + H]^+$ 410 |
| 17 | 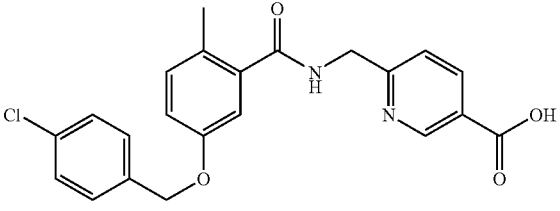 | Heated at 90° C. for 6 hours. Heating continued for 8 hours. Reaction mixture allowed to cool and then evaporated in vacuo. Purified by MDAP.<br>MS $[C_{22}H_{19}{}^{35}ClN_2O_4 M + H]^+$ 411 |
| 18 | 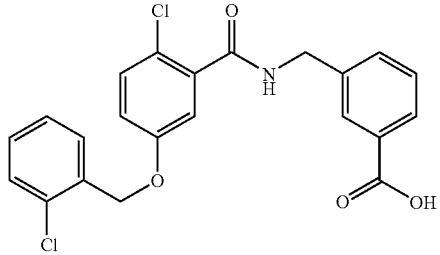 | Reagent used was 4M HCl in dioxane, mixture stirred at room temp for 3 days, solvent evaporated in vacuo, residue purified by MDAP<br>MS $[C_{22}H_{17}{}^{35}Cl_2NO_4 M + H]^+$ 430 |

-continued

| Ex No | | Comments and MS |
|---|---|---|
| 19 | 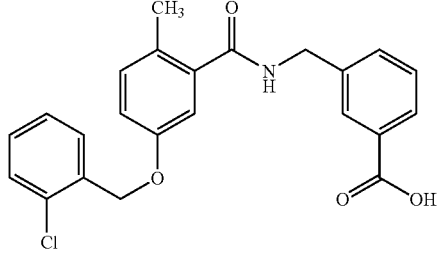 | Reagent used was 4M HCl in dioxane, mixture stirred at room temp for 3 days, solvent evaporated in vacuo, residue purified by MDAP<br>MS $[C_{23}H_{20}{}^{35}ClNO_4$ M + H$]^+$ 410 |

EXAMPLE 20

4-[({[2-chloro-5-({[3-(methyloxy)phenyl] methyl}oxy)phenyl]carbonyl}amino)methyl]benzoic acid

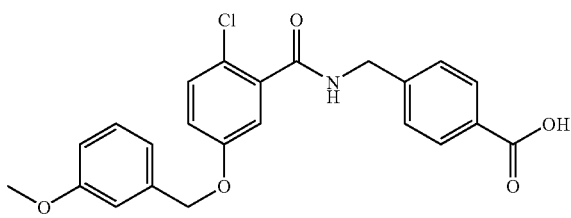

A solution of methyl 4-[({[2-chloro-5-({[3-(methyloxy)phenyl]methyl}oxy)phenyl]carbonyl}amino)methyl]benzoate (106 mg, 0.24 mmol) and lithium hydroxide (2 eq, 20 mg, 0.48 mmol) in dioxane (3 ml) and H$_2$O (1.5 ml) was heated at 65° C. for 3 hours. On cooling solvent was evaporated in vacuo, residue acidified with 2M HCl and filtered to give the title compound as a white solid. MS (ES+) m/z 426 [M+H]$^+$ ($C_{23}H_{20}{}^{35}ClNO_5$). $^1$H-NMR (400 MHz, d$_6$-DMSO) δ 3.76 (3H, s), 4.50 (2H, d, J 6), 5.12 (2H, s), 6.91 1H, dd, J 1.6, J 7.6), 7.02 (1H, s), 7.09 (2H, m), 7.30 (1H, t, J 4), 7.40-7.47 (2H, m), 7.92 (2H, d, J 8), 9.04 (1H, t, J 6)

The following examples 21 to 29 were prepared by a similar two-step method to 4-[({[2-chloro-5-({[3-(methyloxy)phenyl]methyl}oxy)phenyl]carbonyl}amino)methyl]benzoic acid (example 20) from the appropriate intermediate with any differences from the described procedure noted in the following table:

| Ex No | | Comments and MS |
|---|---|---|
| 21 | 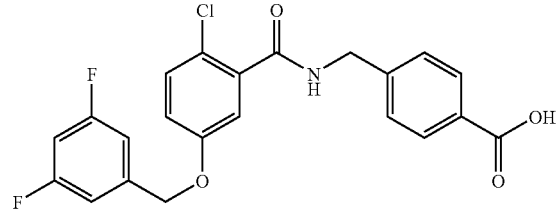 | Mixture stirred at room temperature then heated for 2 hours at 65° C.<br>MS $[C_{22}H_{16}{}^{35}ClF_2NO_4$ M + H$]^+$ 432 |
| 22 | 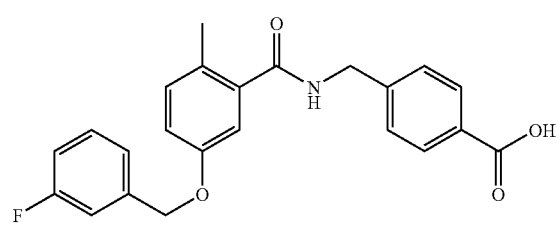 | Heated at 65° C. overnight<br>MS $[C_{23}H_{20}FNO_5$ M + H$]^+$ 394 |
| 23 | 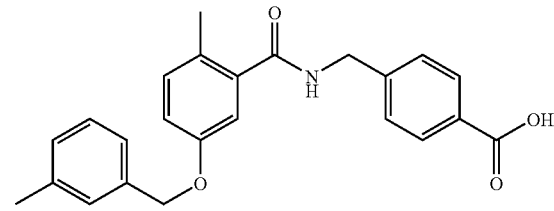 | Heated at 65° C. overnight<br>MS $[C_{24}H_{23}NO_4$ M + H$]^+$ 390 |

| Ex No | | Comments and MS |
|---|---|---|
| 24 | 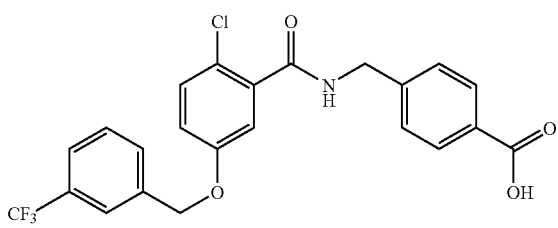 | Heated at 65° C. overnight<br>MS $[C_{23}H_{17}{}^{35}ClF_3NO_4$ M + H$]^+$ 464 |
| 25 | 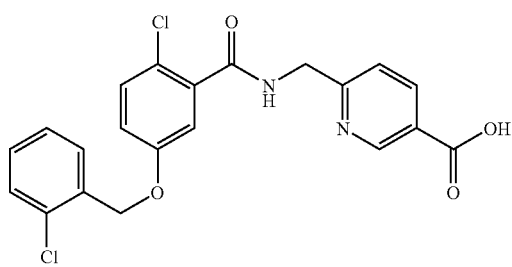 | Stirred at room temperature overnight, work up as example 20 then further purification by MDAP required<br>MS $[C_{21}H_{16}{}^{35}Cl_2N_2O_4$ M + H$]^+$ 431 |
| 26 | 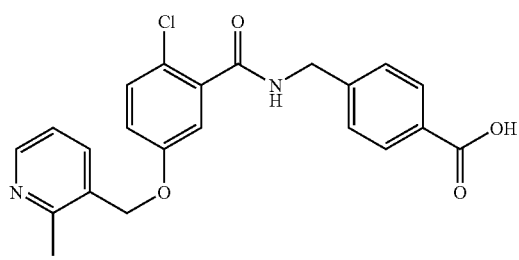 | Stirred at room temperature overnight, work up as example 20 then further purification by MDAP required<br>MS $[C_{22}H_{19}{}^{35}ClN_2O_4$ M + H$]^+$ 411 |
| 27 | 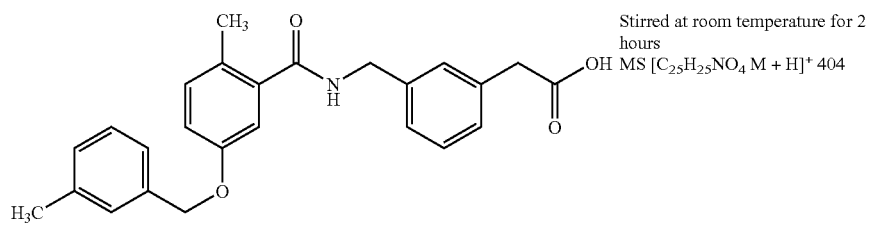 | Stirred at room temperature for 2 hours<br>MS $[C_{25}H_{25}NO_4$ M + H$]^+$ 404 |
| 28 | 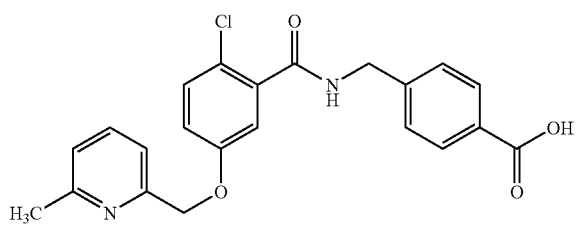 | Stirred at room temperature for 3 hours. Attempt to filter solid failed so mixture evaporated in vacuo and purified by MDAP<br>MS $[C_{22}H_{19}{}^{35}ClN_2O_4$ M + H$]^+$ 411 |
| 29 | 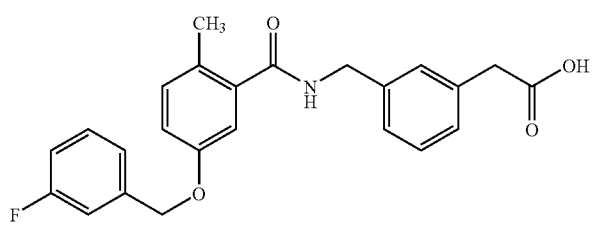 | Stirred at room temperature for 2 hours, work up as example 20, then further purification by trituration with DCM<br>MS $[C_{24}H_{22}FNO_4$ M + H$]^+$ 408 |

EXAMPLE 30

2-chloro-5-{[(3-chlorophenyl)methyl]oxy}-N-{[4-(tetrazol-5-yl)phenyl]methyl}benzamide

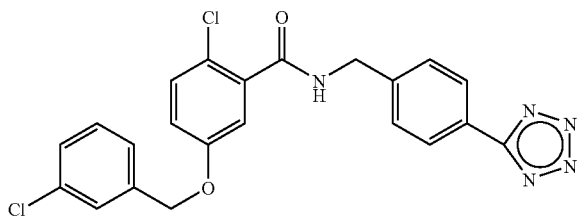

Azidotrimethylsilane (0.027 ml, 0.20 mmol) was added dropwise to a stirred solution of trimethylaluminium in toluene (2M, 0.102 ml, 0.20 mmol) at 0° C. under an atmosphere of argon. A suspension of intermediate 47 (36 mg, 0.09 mmol) in toluene (2 ml) was then added, and the reaction heated to 80° C. After stirring for 17 hours at this temperature, the reaction was cooled and poured into 6N HCl (10 ml) and ethyl acetate (10 ml). The layers were separated and the aqueous phase extracted with further ethyl acetate (2×10 ml). The combined organic layers were washed with brine (10 ml), dried over sodium sulphate, filtered and concentrated to give an off-white solid which was purified by MDAP to give the title compound as a white solid (18 mg). LC (5 min) 2.88, MS (ES+) m/z 454 [M+H]$^+$ ($C_{22}H_{17}{}^{35}Cl_2N_5O_2$). $^1$H-NMR (400 MHz, d$_6$-DMSO) δ 4.52 (2H, d, J 6), 5.18 (2H, s), 7.10-7.16 (2H, m), 7.39-7.60 (7H, m), 8.02 (2H, d, J 8), 9.07 (1H, t, J 6).

Biological Data
In vitro cAMP Assay

Studies were performed using HEK-293(T) cells expressing the recombinant human prostanoid EP$_4$ receptor (HEK-EP$_4$ cells). Cells were grown as a monolayer culture in DMEM-F12/F12 containing glutamax II (Gibco) and supplemented with 10% foetal bovine serum (Gibco) and 0.4 mg.ml-1 G418. HEK-EP$_4$ cells were pre-treated 24 hr and 30 mins prior to the experiment with 10 μM indomethacin and harvested using Versene containing 10 μM indomethacin. The cells were resuspended in assay buffer (DMEM:F12, 10 μM indomethacin and 200 μM IBMX) at 1×10$^6$ cells per ml and incubated for 20 min at 37° C. Thereafter, 50 μl of cells were added to 50 μl agonist (compound of Formula (I)) and incubated at 37° C. for 4 minutes before stopping reactions with 100 μl of 1% triton X-100. cAMP levels in the cell lysates were determined using a competition binding assay. In this assay the ability of cell lysates to inhibit 3H-cAMP (Amersham) binding to the binding subunit of protein kinase A was measured and cAMP levels were calculated from a standard curve. The data for each compound were expressed as a % of the response to a 10 nM maximal concentration of the standard agonist PGE2. For each compound the maximal response and concentration of compound causing 50% of its maximal response were calculated.

Intrinsic activity is expressed relative to the maximal response to PGE2. Unless stated, reagents were purchased commercially from Sigma.

The Examples of the present invention were tested in the above-mentioned assay and exhibited average pEC$_{50}$ values of 6.43 or higher, and average intrinsic activities of 17.4 or higher.

The invention claimed is:
1. A compound of formula (I) or pharmaceutically acceptable salts thereof,

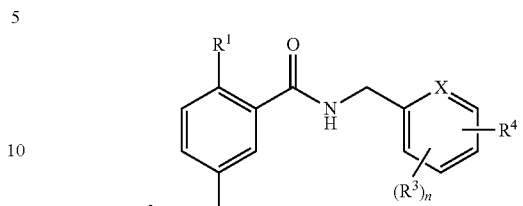

wherein
R$^1$ is H, or halo or C$_{1-4}$ alkyl;
R$^2$ is a 4 to 6 membered non-aromatic carbocylic group, or phenyl, or pyridinyl;
which carbocylic or pyridinyl group is optionally substituted with one or two substituents, which may be the same or different, selected from the group consisting of: halo, C$_{1-4}$ alkyl, C$_{1-4}$ alkoxy, halo C$_{1-4}$ alkyl and halo C$_{1-4}$ alkoxy;
or which phenyl group is substituted with one or two substituents, which may be the same or different, selected from the group consisting of: halo, C$_{1-4}$ alkyl, C$_{1-4}$ alkoxy, halo C$_{1-4}$ alkyl and halo C$_{1-4}$ alkoxy;
R$^3$ is halo;
R$^4$ is COOH, CH$_2$COOH or tetrazolyl;
X is C or N; and
n is 0 or 1;
with the proviso that when R$^4$ is in the 4 position on the ring, it cannot be CH$_2$COOH; and
when R$^4$ is in the 3 position on the ring, R$^2$ is not 4-chlorophenyl.

2. A compound of formula (I) according to claim 1 or a pharmaceutically acceptable salt thereof wherein R$^1$ is chloro.

3. A compound of formula (I) according to claim 1 or a pharmaceutically acceptable salt thereof wherein R$^2$ is phenyl substituted with one or two substituents, which may be the same or different, selected from the group consisting of halo, C$_{1-4}$ alkyl, C$_{1-4}$ alkoxy, halo C$_{1-4}$ alkyl and halo C$_{1-4}$ alkoxy.

4. A compound of formula (I) according to claim 1 selected from the group consisting of:
4-({[(2-chloro-5-{[(2-chlorophenyl)methyl]oxy{phenyl)carbonyl]amino}methyl)benzoic acid;
4-({[(2-chloro-5-{[(3-chlorophenyl)methyl]oxy}phenyl)carbonyl]amino}methyl)benzoic acid;
3-({[(2-chloro-5-{[(3-chlorophenyl)methyl]oxy}phenyl)carbonyl]amino}methyl)benzoic acid;
6-({[(2-chloro-5-{[(3-chlorophenyl)methyl]oxy}phenyl)carbonyl]amino}methyl)-3-pyridinecarboxylic acid;
4-({[(5-{[(3-chlorophenyl)methyl]oxy}-2-methylphenyl)carbonyl]amino}methyl)benzoic acid;
5-({[(2-chloro-5-{[(3-chlorophenyl)methyl]oxy}phenyl)carbonyl]amino}methyl)-2-fluorobenzoic acid;
[3-({[(2-chloro-5-{[(3-chlorophenyl) methyl]oxy}phenyl)carbonyl]amino}methyl)phenyl]acetic acid;
4-({[(5-{[(3-chlorophenyl)methyl]oxy}-2-fluorophenyl)carbonyl]amino}methyl)benzoic acid;
4-({[(2-chloro-5-{[(3-fluorophenyl)methyl]oxy}phenyl)carbonyl]amino}methyl)benzoic acid;
4-({[(2-chloro-5-{[(3-methylphenyl)methyl]oxy}phenyl)carbonyl]amino}methyl)benzoic acid;

4-({[(2-chloro-5-{[(4-chlorophenyl)methyl]oxy}phenyl)carbonyl]amino}methyl)benzoic acid;

4-{[({2-chloro-5-[(cyclohexylmethyl)oxy]phenyl}carbonyl)amino]methyl}benzoic acid;

4-{[({2-chloro-5-[(cyclobutylmethyl)oxy]phenyl}carbonyl)amino]methyl}benzoic acid;

6-({[(5-{[(3-chlorophenyl)methyl]oxy}-2-methylphenyl)carbonyl]amino}methyl)-3-pyridinecarboxylic acid;

[3-({[(5-{[(3-chlorophenyl)methyl]oxy}-2-methylphenyl)carbonyl]amino}methyl)phenyl]acetic acid;

3-({[(5-{[(3-chlorophenyl)methyl]oxy}-2-methylphenyl)carbonyl]amino}methyl)benzoic acid;

6-({[(5-{[(4-chlorophenyl)methyl]oxy}-2-methylphenyl)carbonyl]amino}methyl)-3-pyridinecarboxylic acid;

3-({[(2-chloro-5-{[(2-chlorophenyl)methyl]oxy}phenyl)carbonyl]amino}methyl)benzoic acid;

3-({[(5-{[(2-chlorophenyl)methyl]oxy}-2-methylphenyl)carbonyl]amino}methyl)benzoic acid;

4-[({[2-chloro-5-({[3-(methyloxy)phenyl]methyl}oxy)phenyl]carbonyl}amino)methyl]benzoic acid;

4-({[(2-chloro-5-{[(3,5-difluorophenyl)methyl]oxy}phenyl)carbonyl]amino}methyl)benzoic acid;

4-({[(5-{[(3-fluorophenyl)methyl]oxy}-2-methylphenyl)carbonyl]amino}methyl)benzoic acid;

4-({[(2-methyl-5-{[(3-methylphenyl)methyl]oxy}phenyl)carbonyl]amino}methyl)benzoic acid;

4-[({[2-chloro-5-({[3-(trifluoromethyl)phenyl]methyl}oxy)phenyl]carbonyl}amino)methyl]benzoic acid;

6-({[(2-chloro-5-{[(2-chlorophenyl)methyl]oxy}phenyl)carbonyl]amino}methyl)-3-pyridinecarboxylic acid;

4-({[(2-chloro-5-{[(2-methyl-3-pyridinyl)methyl]oxy}phenyl)carbonyl]amino}methyl)benzoic acid;

[3-({[(2-methyl-5-{[(3-methylphenyl)methyl]oxy}phenyl)carbonyl]amino}methyl)phenyl]acetic acid;

4-({[(2-chloro-5-{[(6-methyl-2-pyridinyl)methyl]oxy}phenyl)carbonyl]amino}methyl)benzoic acid;

[3-({[(5-{[(3-fluorophenyl)methyl]oxy}-2-methylphenyl)carbonyl]amino}methyl)phenyl]acetic acid;

2-chloro-5-{[(3-chlorophenyl)methyl]oxy}-N-{[4-(1H-tetrazol-5-yl)phenyl]methyl}benzamide;

4-{[({2-methyl-5-[(phenylmethyl)oxy]phenyl}carbonyl)amino]methyl}benzoic acid; and 4-{[({2-fluoro-5-[(phenylmethyl)oxy]phenyl}carbonyl)amino]methyl}benzoic acid, or a pharmaceutically acceptable salt thereof.

5. A pharmaceutical composition comprising a compound of formula (I) as defined in claim 1 or its pharmaceutically acceptable salt and a pharmaceutically acceptable carrier, excipient or diluent.

* * * * *